(12) United States Patent
Nishimura et al.

(10) Patent No.: US 8,586,547 B2
(45) Date of Patent: Nov. 19, 2013

(54) CDC45L PEPTIDES AND VACCINES INCLUDING THE SAME

(75) Inventors: Yasuharu Nishimura, Kumamoto (JP); Yusuke Tomita, Kumamoto (JP); Yusuke Nakamura, Tokyo (JP); Takuya Tsunoda, Kanagawa (JP)

(73) Assignee: Oncotherapy Science, Inc., Kanagawa (JP)

( * ) Notice: Subject to any disclaimer, the term of this patent is extended or adjusted under 35 U.S.C. 154(b) by 0 days.

(21) Appl. No.: 13/321,812

(22) PCT Filed: May 25, 2010

(86) PCT No.: PCT/JP2010/003488
§ 371 (c)(1),
(2), (4) Date: Mar. 9, 2012

(87) PCT Pub. No.: WO2010/137295
PCT Pub. Date: Dec. 2, 2010

(65) Prior Publication Data
US 2012/0164163 A1 Jun. 28, 2012

Related U.S. Application Data

(60) Provisional application No. 61/217,133, filed on May 26, 2009.

(51) Int. Cl.
*A61K 38/08* (2006.01)
*A61K 38/04* (2006.01)

(52) U.S. Cl.
USPC .......................................... 514/21.6; 530/328

(58) Field of Classification Search
None
See application file for complete search history.

(56) References Cited

U.S. PATENT DOCUMENTS

| | | |
|---|---|---|
| 6,913,919 B2 * | 7/2005 | Botstein et al. ............. 435/252.3 |
| 2006/0216301 A1 | 9/2006 | Tahara et al. |
| 2009/0149333 A1 | 6/2009 | Knudsen et al. |
| 2009/0208514 A1 | 8/2009 | Nakamrua et al. |
| 2009/0317392 A1 | 12/2009 | Nakamura et al. |
| 2010/0152421 A1 | 6/2010 | Nishimura et al. |

FOREIGN PATENT DOCUMENTS

| | | |
|---|---|---|
| JP | 2007-167058 A | 7/2007 |
| WO | WO 2004/024766 A1 | 3/2004 |
| WO | WO 2007/013665 A1 | 2/2007 |
| WO | WO 2007/013671 A1 | 2/2007 |
| WO | WO 2007/145318 A1 | 12/2007 |
| WO | WO 2008/081581 A1 | 7/2008 |

OTHER PUBLICATIONS

Rosenberg et. al. Nature Medicine 10:909-915.*
Xu et al., 2012. Vaccine, 30: 2805-2810.*
Frankenberg et al., 2012. Eur. J. Cell Biol. 91:53-58.*
Robson et al., 2010. Curr. Opin. Immunol. 22:137-144.*
Schuler et al., 2003. Curr. Opin. Immunol. 15: 138-147.*
Parmiani et al., 2002. J. Natl. Ca. Inst., 94, 805-818.*
Leggatt et al J Immunology 161: 4728-4735, 1998.*
Shaikh et al. 1999. Mammalian Genome 10:322-326.*
Aparicio, T., et al., "The human GINS complex associates with Cdc45 and MCM and is essential for DNA replication," *Nucleic Acids Research*, vol. 37(7), pp. 2087-2095 (Apr. 2009, Epub Feb. 17, 2009).
Bauerschmidt, C., et al., "Interactions of human Cdc45 with the Mcm2-7 complex, the CINS complex, and DNA polymerases δ and ε during S phase," *Genes to Cells*, vol. 12(6), pp. 745-758 (Jun. 2007).
Brichard, V., et al., "GSK's antigen-specific cancer immunotherapy programme: Pilot results leading to Phase III clinical development," *Vaccine*, vol. 25, Suppl. 2, pp. B61-B71 (Sep. 27, 2007).
Bunn, P., et al., "Conclusion," *Oncologist*, vol. 13, Suppl. 1, pp. 37-46 (2008).
Feng, D., et al., "Inhibiting the Expression of DNA Replication-Initiation Proteins Induces Apoptosis in Human Cancer Cells," *Cancer Research*, vol. 63(21), pp. 7356-7364 (Nov. 1, 2003).
Fukushima, S., et al., "Multiple Antigen-targeted Immunotherapy With α-Galactosylceramide-loaded and Genetically Engineered Dendritic Cells Derived From Embryonic Stem Cells," *J. Immunother.*, vol. 32(3), pp. 219-231 (Apr. 2009).
Hall, P., et al., "Stem cells: the generation and maintenance of cellular diversity," *Development*, vol. 106(4), pp. 619-633 (Aug. 1989).
Harao, M., et al., "HLA-A2-restricted CTL epitopes of a novel lung cancer-associated cancer testis antigen, cell division cycle associated 1, can induce tumor-reactive CTL," *Int. J. Cancer*, vol. 123(11), pp. 2616-2625 (Dec. 1, 2008).
Hasegawa, S., et al., "Genome-Wide Analysis of Gene Expression in Intestinal-Type Gastric Cancers Using a Complementary DNA Microarray Representing 23, 040 Genes," *Cancer Research*, vol. 62(23), pp. 7012-7017 (Dec. 1, 2002).
Hirschowitz, E., et al., "Immunotherapy for Lung Cancer," *Proc. Am. Thorac. Soc.*, vol. 6(2), pp. 224-232 (Apr. 15, 2009).
Imai, K., et al., "Identification of a Novel Tumor-Associated Antigen, Cadherin 3/P-Cadherin, as a Possible Target for Immunotherapy of Pancreatic, Gastric, and Colorectal Cancers," *Clinical Cancer Research*, vol. 14(20), pp. 6487-6495 (Oct. 15, 2008).
Li, J., et al., "mRNA expression of the DNA replication-initiation proteins in epithelial dysplasia and squamous cell carcinomas of the tongue," *BMC Cancer*, vol. 8(395), 8 pgs. (Dec. 30, 2008).
Mathiassen, S., et al., "Tumor-associated antigens identified by mRNA expression profiling induce protective anti-tumor immunity," *Eur. J. Immunol.*, vol. 31(4), pp. 1239-1246 (Apr. 2001).

(Continued)

*Primary Examiner* — Shulamith H Shafer
(74) *Attorney, Agent, or Firm* — Kilpatrick Townsend & Stockton LLP

(57) ABSTRACT

The present invention provides isolated peptides or the fragments derived from SEQ ID NO: 18, which bind to an HLA antigen and induce cytotoxic T lymphocytes (CTL). The peptides may include one of the above mentioned amino acid sequences with substitution, deletion, or addition of one, two, or several amino acids sequences. The present invention also provides pharmaceutical compositions including these peptides. The peptides of the present invention can be used for treating cancer.

10 Claims, 11 Drawing Sheets

(56) References Cited

OTHER PUBLICATIONS

Miyata, H., et al., "CDC25B and p53 Are Independently Implicated in Radiation Sensitivity for Human Esophageal Cancers," *Clinical Cancer Research*, vol. 6(12), pp. 4859-4865 (Dec. 2000).

Parkin, D., et al., "Global Cancer Statistics, 2002," *CA Cancer J Clin.*, vol. 55(2), pp. 74-108 (Mar.-Apr. 2005).

Pollok, S., et al., "Cdc45 degradation during differentiation and apoptosis," *Biochem Biophys Res Commun*, vol. 362(4), pp. 910-915 (Nov. 3, 2007, Epub Aug. 22, 2007).

Pollok, S., et al., Human Cdc45 is a proliferation-associated antigen, *FEBS*, vol. 274(14), pp. 3669-3684 (Jul. 2007, Epub Jul. 3, 2007).

Romero, P., Current State of Vaccine Therapies in Non-Small-Cell Lung Cancer, *Clin Lung Cancer*, vol. 9, Suppl. 1, pp. S28-S36 (Feb. 2008).

Ruttinger, D., et al., "Current Immunotherapeutic Strategies in Lung Cancer," *Surg. Oncol. Clin N. Am.*, vol. 16(4), pp. 901-918 (Oct. 2007).

Saha, P., et al., "The Human Homolog of *Saccharomyces cerevisiae* CDC45," *J. Biol., Chem.*, vol. 273(29), pp. 18205-18209 (Jul. 17, 1998).

Schmidt, S., et al., "Induction of Adipophilin-Specific Cytotoxic T Lymphocytes Using a Novel HLA-A2-Binding Peptide That Mediates Tumor Cell Lysis," *Cancer Research*, vol. 64(3), pp. 1164-1170 (Feb. 1, 2004).

Stevanovic, S., "Identification of Tumor-Associated T-Cell Epitopes for Vaccine Development," *Nat. Rev. Cancer*, vol. 2(7), pp. 514-520 (Jul. 2002).

Tomita, Y., et al., "Identification of a novel tumor-associated antigen CDC45L which is useful for immunotherapy of lung cancer," *Proceedings of the 13th Annual Meeting of the Japanese Society of Cancer Immunology*, p. 79 (May 20, 2009).

Tomita, Y., et al., "Identification of a novel tumor-associated antigen CDC45L, as a candidate of target for immunotherapy of lung cancer," *Proceedings of the 68th Annual Meeting of the Japanese Cancer Association*, vol. 68, p. 295, Abstract P-0585 (2009).

Yamabuki, T., et al., "Genome-wide gene expression profile analysis of esophageal squamous cell carcinomas," *International Journal of Oncology*, vol. 28(6), pp. 1375-1384 (Jun. 2006).

Yamabuki, T., et al., "Isolation and characterization of a novel gene IMS-ESO1 as a therapeutic target for esophageal squamous-cell carcinoma," *Proceedings of the 64th Annual Meeting of the Japanese Cancer Association*, vol. 64, p. 525, Abstract W-821 (2005).

Yokomine, K., et al., "The forkhead box M1 transcription factor as a candidate of target for anti-cancer immunotherapy," *Int. J. Cancer*, vol. 126(9), pp. 2153-5163 (May 1, 2010).

Zhang, C., et al., "Changes in gene expression that accompany the immortalization or transformation of human bronchial epithelial cells," *Proc. Amer. Assoc. Cancer Res.*, vol. 45, Abstract #1720, 2 pgs (2004).

Database Genbank: HD691104, "Sequence 567820 from Patent EP2213738," 1 pg. (Aug. 18, 2010, downloaded from http://www.ncbi/nlm.gov/nuccore/303961968?report=genbank on Jan. 20, 2012).

U.S. Appl. No. 13/246,639, filed Sep. 27, 2011, 164 pgs.

U.S. Appl. No. 13/389,798, which is a U.S. National Phase Application of PCT/JP2010/005049 filed Aug. 12, 2010, 105 pgs.

Dionne, et al., "Her-2/neu altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).

Falk, et al., "Allele-specific motifs revealed by sequencing of self-peptides eluted from MHC molecules," *Nature*, vol. 351(6324), pp. 290-296 (May 23, 1991).

Hoffman, et al., "The Ability of Variant Peptides to Reverse the Nonresponsiveness of T Lymphocytes to the Wild-Type Sequence $p53_{264-272}$ Epitope," *J Immunol.*, vol. 168(3), pp. 1338-1347 (Feb. 1, 2002).

Kondo, et al., Prominent Roles of Secondary Anchor Residues in Peptide Binding to HLA-A24 Human Class I Molecules, *J Immunol.*, vol. 155(9), pp. 4307-4312 (Nov. 1, 1995).

Kubo, et al., "Definition of Specific Peptide Motifs for Four Major HLA-A Alleles," *J Immunol.*, vol. 152(8), pp. 3913-3924 (Apr. 15, 1994).

Rammensee, et al., "MHC ligands and peptide motifs: first listing," *Immunogenetics*, vol. 41(4), pp. 178-228 (1995).

Zaremba, et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).

Ou, et al., "Modification of amino acid substitution of the epitope HPV-16E7$_{11-20}$," *Chinese Journal of Microbiology and Immunology*, vol. 26(11), pp. 990-993 (2006), abstract only.

\* cited by examiner

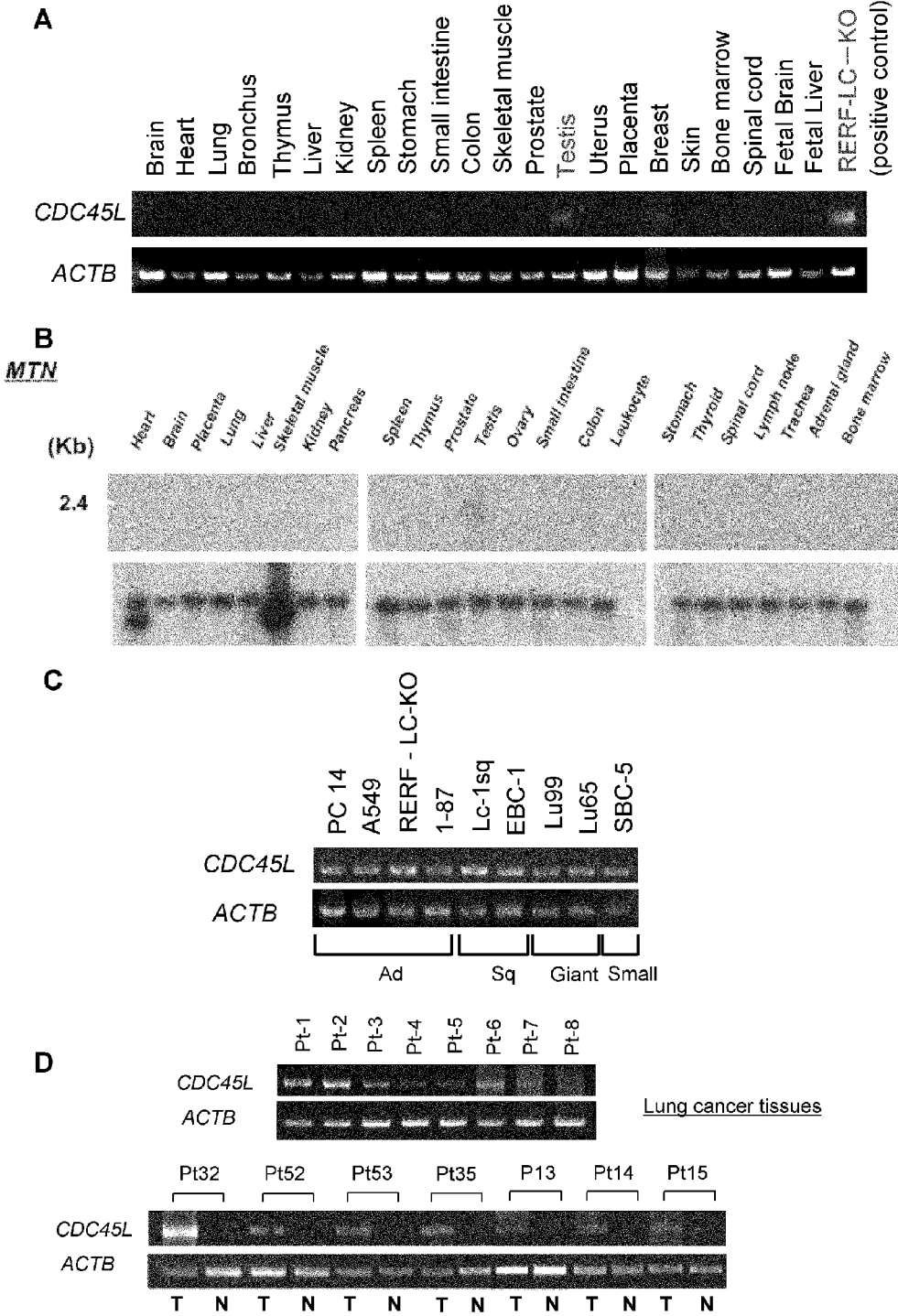
Fig. 1a-d

Fig. 1e-f
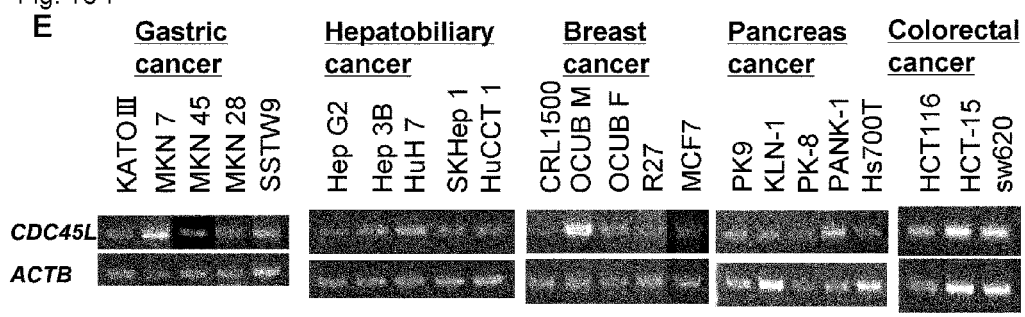
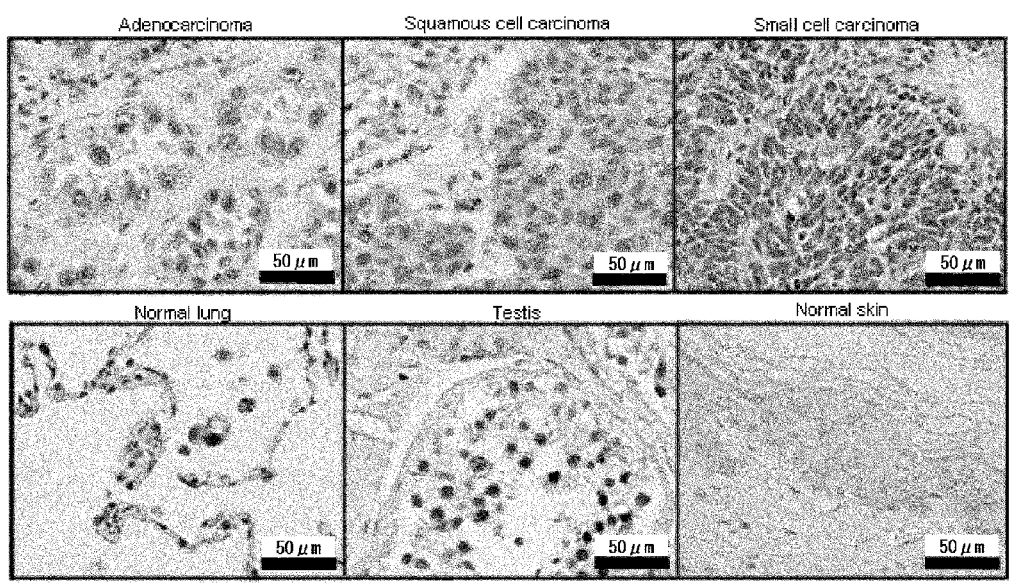

Fig. 3
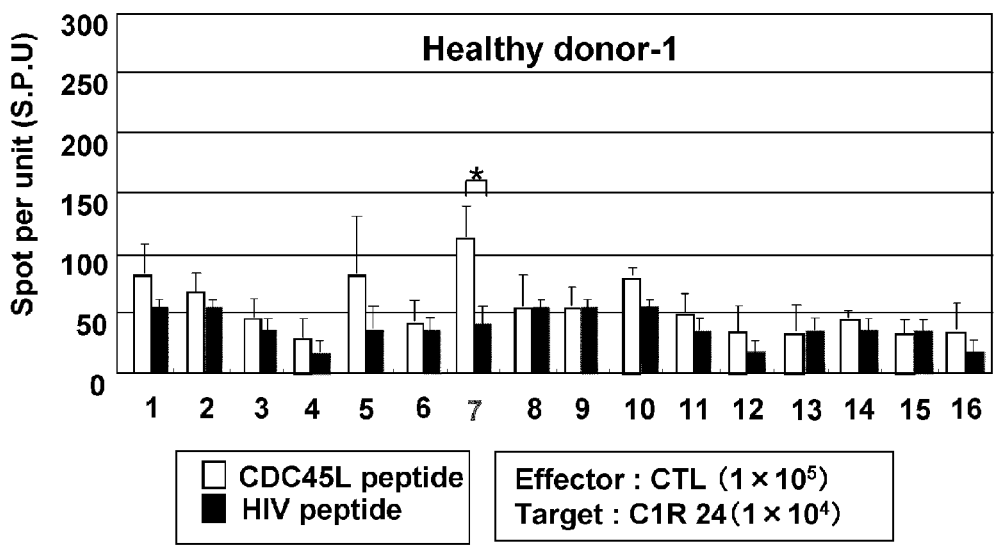
A
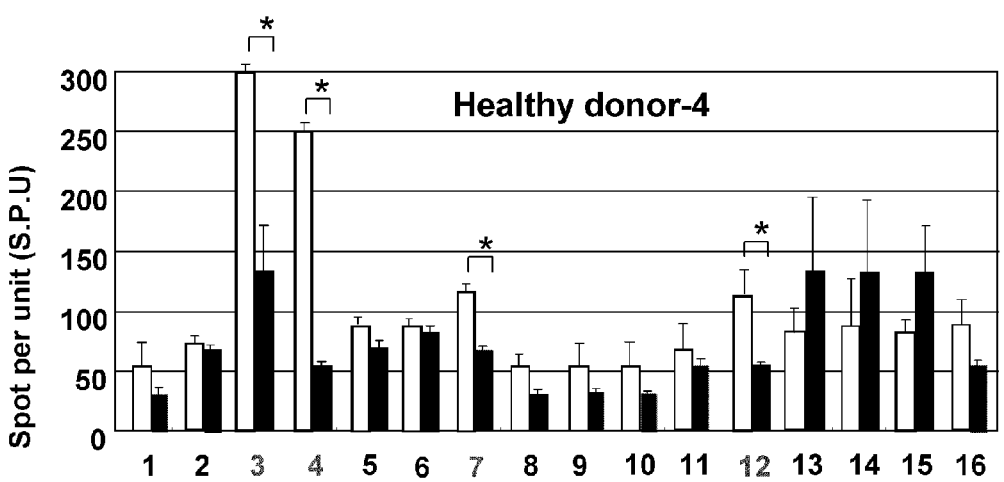
B
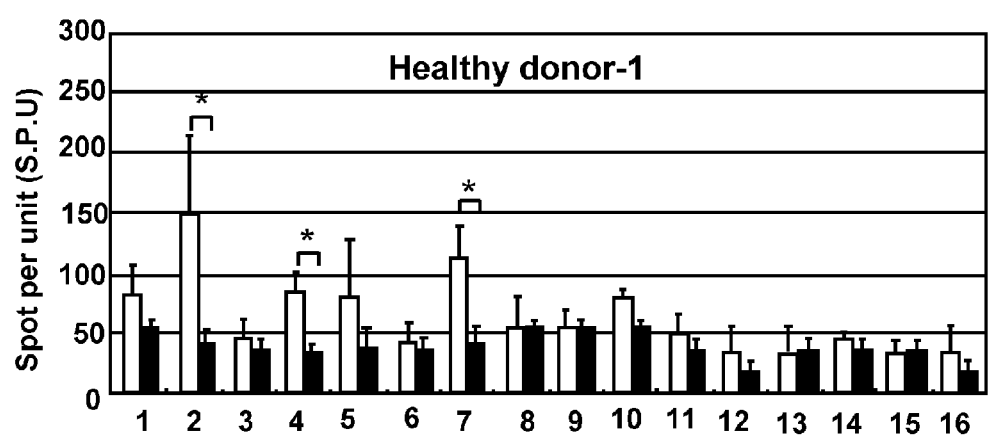
C

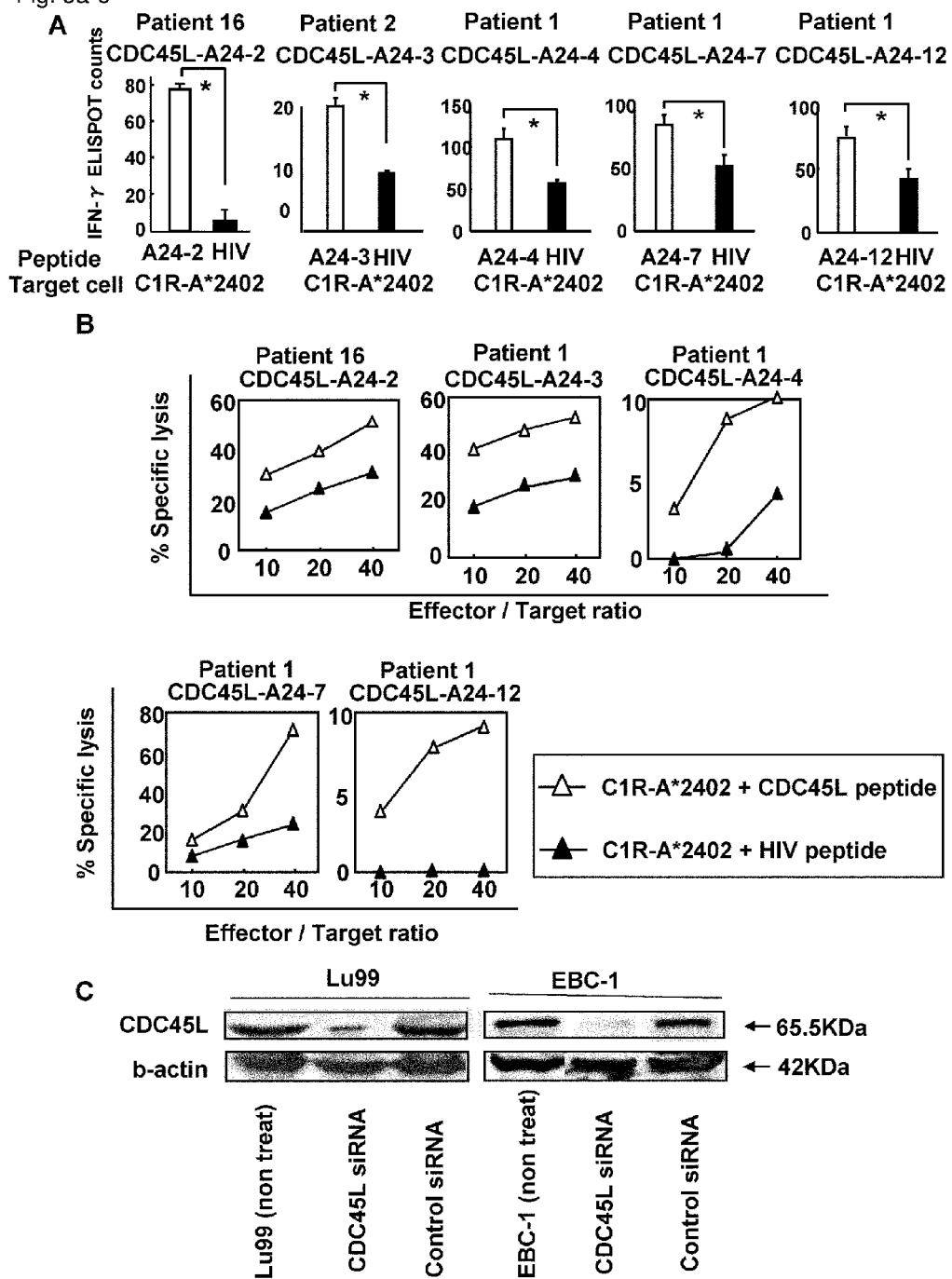
Fig. 5a-c

Fig. 5d
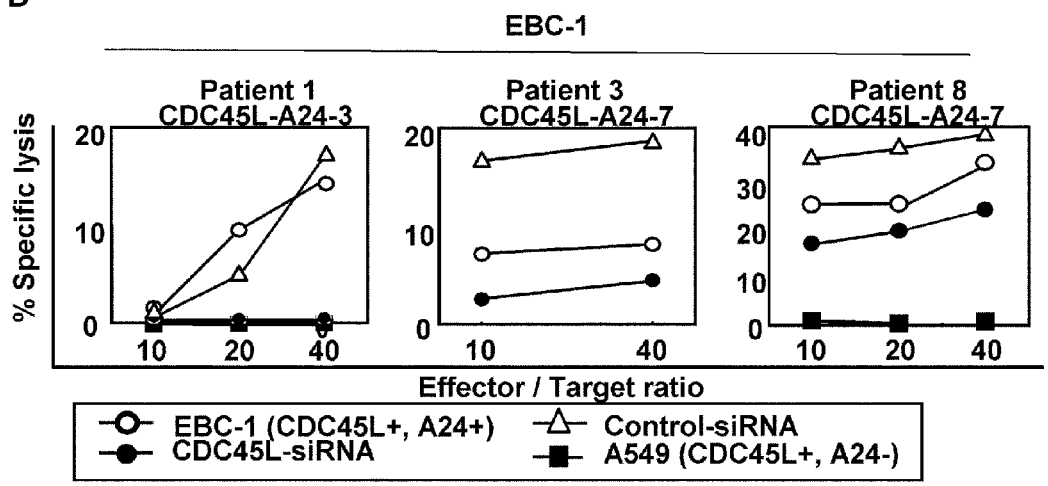
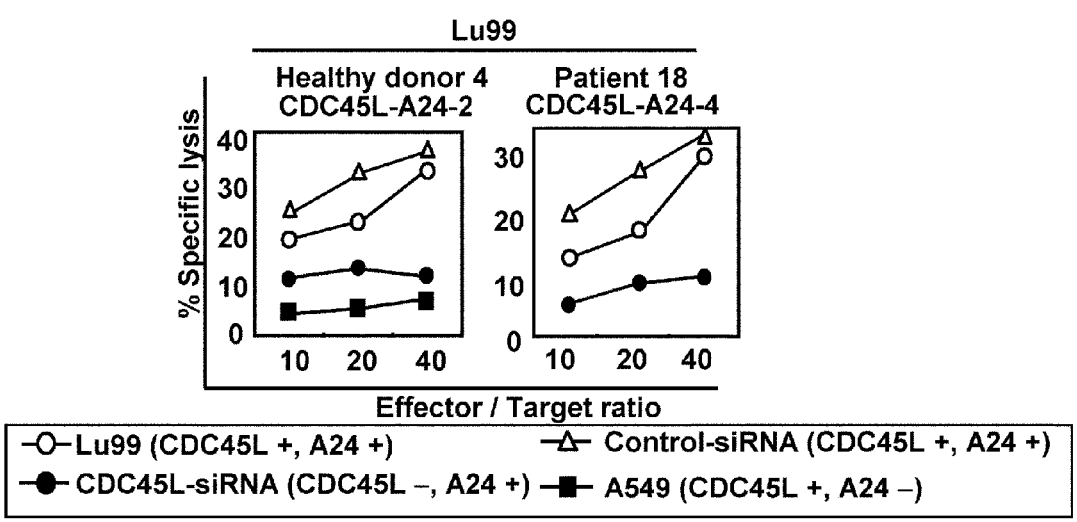

Fig. 6
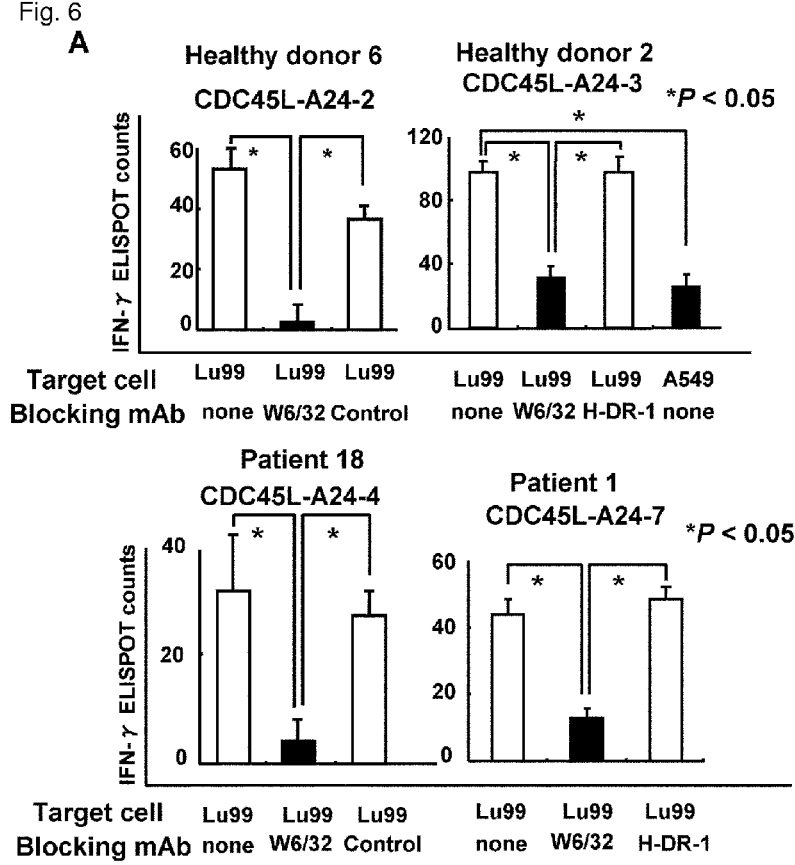
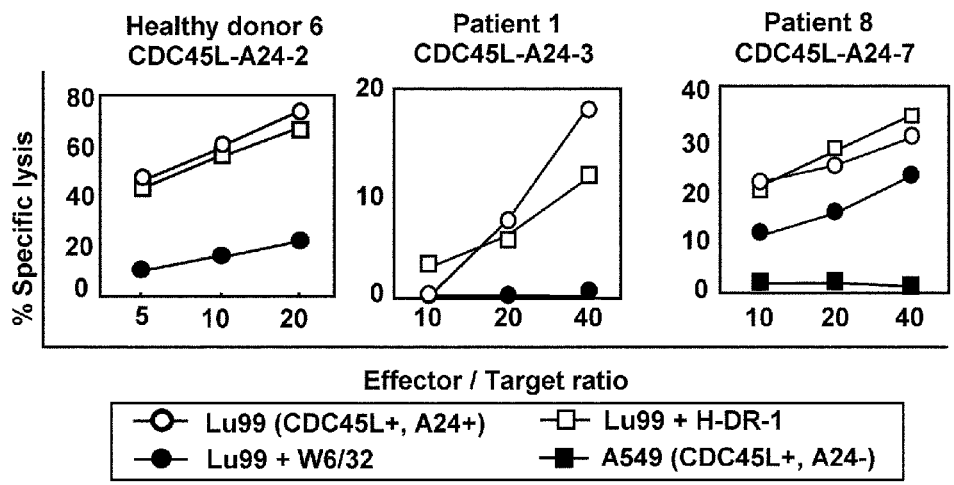

Fig. 8a-b
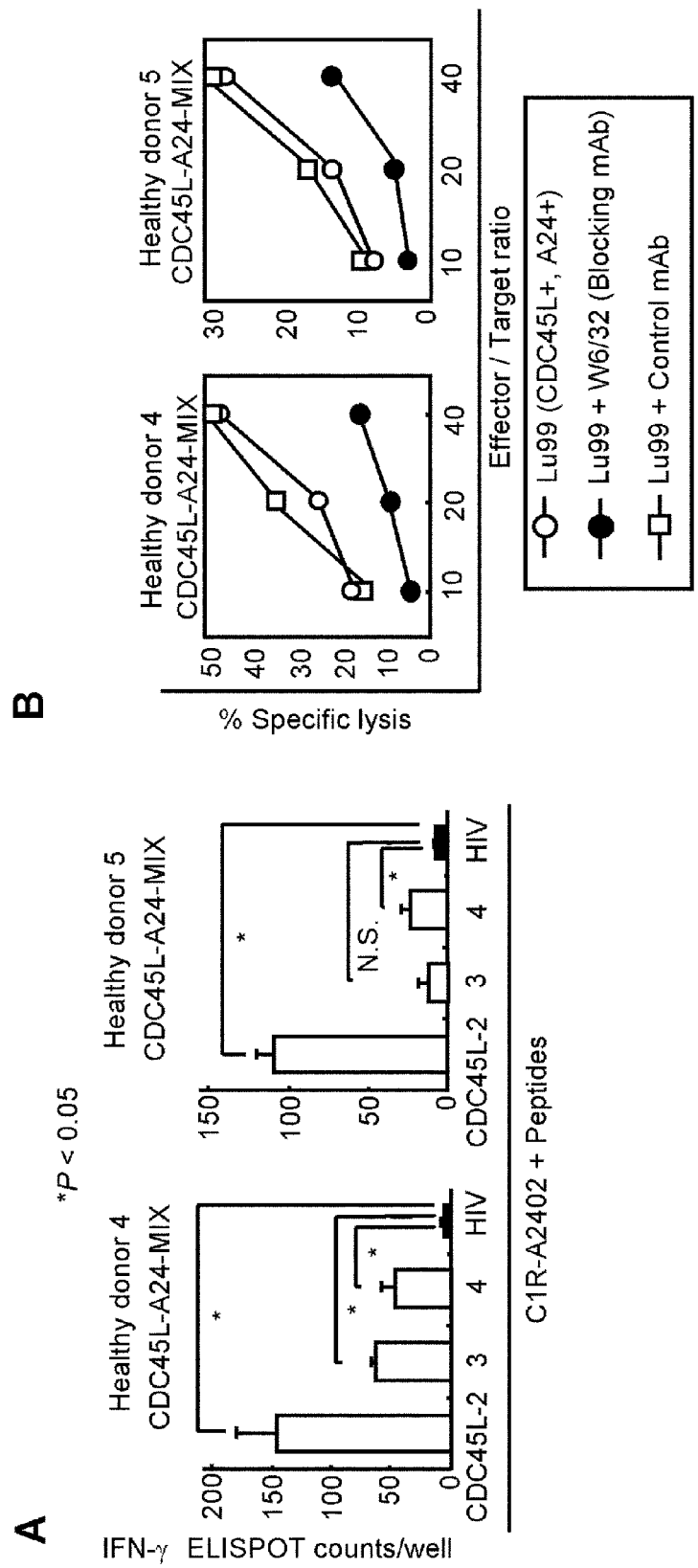

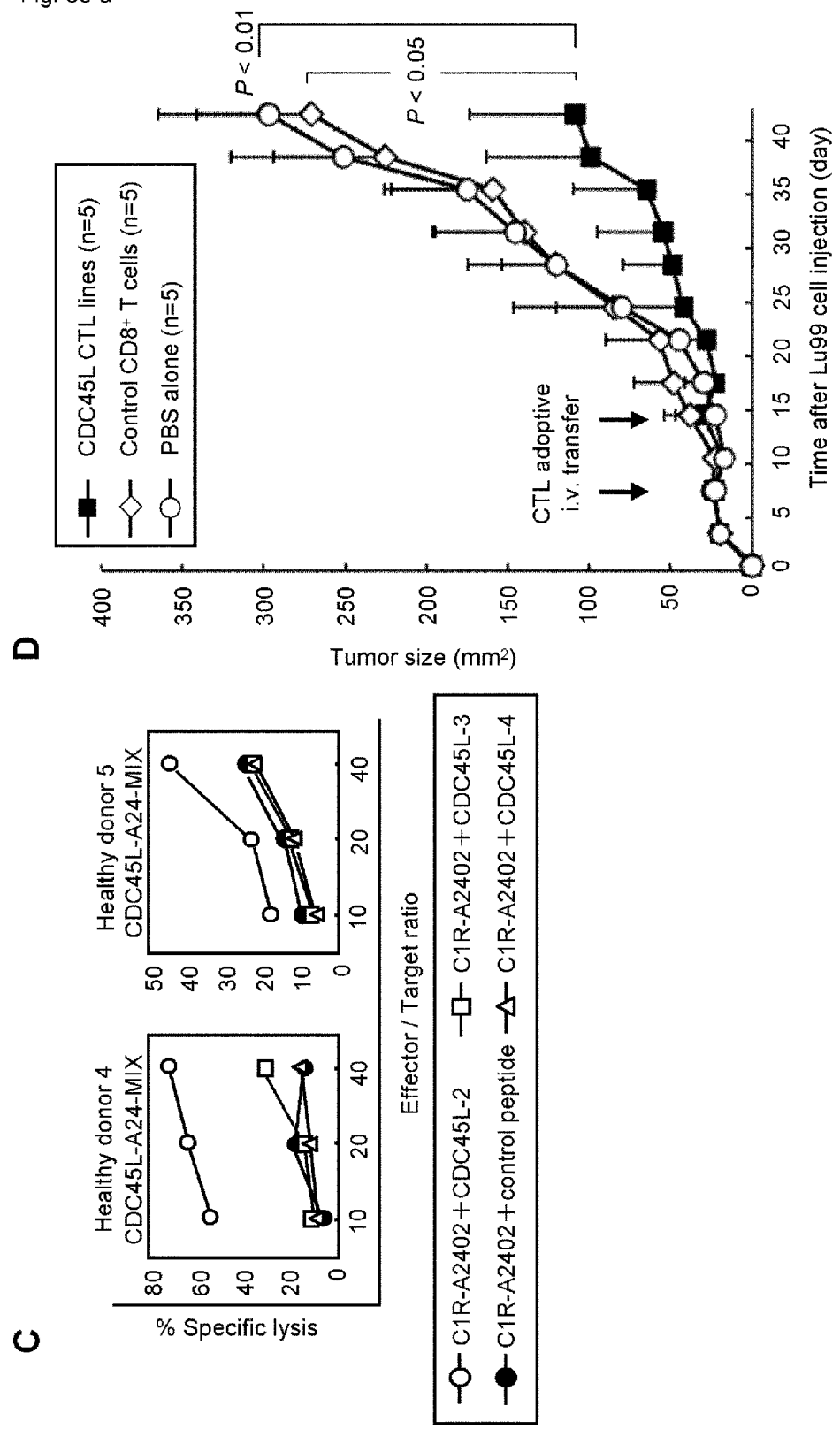
Fig. 8c-d

CDC45L PEPTIDES AND VACCINES INCLUDING THE SAME

PRIORITY

The present application is a U.S. National Phase of PCT/JP2010/003488, filed May 25, 2010, which claims the benefit of U.S. Provisional Applications No. 61/217,133, filed on May 26, 2009, the entire contents of which are incorporated by reference herein in their entirety.

REFERENCE TO A SEQUENCE LISTING

This application includes a Sequence Listing as a text file named "SUB_SEQTXT_87331-824929_019910US.txt" created Mar. 7, 2012, and containing 13,278 bytes. The material contained in this text file is incorporated by reference in its entirety for all purposes.

The present invention relates to the field of biological science, more specifically to the field of cancer therapy. In particular, the present invention relates to novel peptides that are extremely effective as cancer vaccines and drugs for treating and preventing tumors.

BACKGROUND ART

Lung cancer is the most common form of cancer, accounting for 1.35 million of the 10.9 million new cases of cancer per year. It is also the leading cause of death from cancer-associated disease, accounting for 1.18 million of the 6.7 million cancer-related deaths worldwide (NPL 1). Despite recent improvements in systemic therapy, such as chemotherapy and molecular-targeting therapy, the prognosis of patients with advanced-stage lung cancer remains very poor (NPL 2). Lung cancer recurs in 50% of patients after surgery and less than 25% of patients respond to systemic chemotherapy. Accordingly, more effective treatment modalities are urgently required, and immunotherapy represents one promising approach for future lung cancer therapies (NPLs 3-5).

The success of therapeutic cancer vaccines may ultimately rely on the identification of immunogenic antigens that are overexpressed in tumors relative to normal tissues. Effective induction of cytotoxic T lymphocytes (CTLs) by tumor-associated antigen (TAA) has shown promising results (NPLs 6-7). Recently, the development of cDNA microarray technologies, coupled with genome information, has provided comprehensive profiles of the gene expression of malignant cells, which may then be compared with those of normal cells (NPL 8). Gene expression profiling with cDNA microarray technologies constitutes an effective approach for the identification of new TAAs useful for cancer diagnosis and immunotherapy (NPLs 9-12).

Although several candidate TAAs expressed in lung cancer have been published (NPLs 13-14), it is important to identify multiple TAAs overexpressed in a given cancer to develop more effective T cell-mediated cancer immunotherapy (NPL 15).

CDC45L (cell division cycle 45-like) is an essential cellular protein that functions in both the initiation and elongation of DNA replication to ensure that chromosomal DNA is replicated only once per cell cycle (NPLs 16-19). CDC45L is highly conserved among all eukaryotes, and a targeted disruption of this gene causes embryonic lethality in mice (NPL 20). In adult humans, the vast majority of cells has differentiated and ceased cell division, and only a small population of cells is proliferating in some selfrenewing tissues (NPL 21). Thus, while CDC45L is absent in long-term quiescent, terminally differentiated and senescent human cells, it is present throughout the cell cycle of proliferating cancer cells (NPL 18). Accordingly, CDC45L expression is tightly associated with proliferating cell populations, and thus is considered to be a promising candidate for a novel proliferation marker in cancer cell biology (NPLs 18, 22). However, the usefulness of CDC45L as a target for cancer immunotherapy has not yet been fully investigated.

CITATION LIST

Non Patent Literature

[NPL 1] Parkin D M et al. CA Cancer J Clin 2005; 55:74-108
[NPL 2] Bunn P A, Jr. et al. Conclusion. Oncologist 2008; 13 Suppl 1:37-46
[NPL 3] Ruttinger D et al. Surg Oncol Clin N Am 2007; 16:901-18
[NPL 4] Hirschowitz E A et al. Proc Am Thorac Soc 2009; 6:224-32
[NPL 5] Romero P et al. Clin Lung Cancer 2008; 9 Suppl 1:S28-36
[NPL 6] Stevanovic S et al. Nat Rev Cancer 2002; 2:514-20
[NPL 7] Brichard V G et al. Vaccine 2007; 25 Suppl 2:B61-71
[NPL 8] Hasegawa S et al. Cancer Res 2002; 62:7012-7
[NPL 9] Mathiassen S et al. Eur J Immunol 2001; 31:1239-46
[NPL 10] Schmidt S M et al. Cancer Res 2004; 64:1164-70
[NPL 11] Yamabuki T et al. Int J Oncol 2006; 28:1375-84
[NPL 12] Imai K et al. Clin Cancer Res 2008; 14:6487-95
[NPL 13] Harao M et al. Int J Cancer 2008; 123:2616-25
[NPL 14] Yokomine K et al. Int J Cancer 2009; 126:2153-63
[NPL 15] Fukushima S et al. J Immunother 2009; 32:219-31
[NPL 16] Aparicio T et al. Nucleic Acids Res 2009; 37:2087-95
[NPL 17] Saha P et al. J Biol Chem 1998; 273:18205-9
[NPL 18] Pollok S et al. FEBS J 2007; 274:3669-84
[NPL 19] Bauerschmidt C et al. Genes Cells 2007; 12:745-58
[NPL 20] Pollok S et al. Biochem Biophys Res Commun 2007; 362:910-5
[NPL 21] Hall P A et al. Development 1989; 106:619-33
[NPL 22] Li J N et al. BMC Cancer 2008; 8:395

SUMMARY OF INVENTION

The present invention is based, at least in part, on the discovery of peptides that may serves as targets of immunotherapy. Because TAAs are sometimes perceived by the immune system as "self" and therefore often have no immunogenicity, the discovery of appropriate targets is of extreme importance. As noted above, CDC45L (a typical amino acid sequence and gene sequence are shown in SEQ ID NO: 18 and SEQ ID NO: 17, respectively, and the sequences are also available from GenBank Accession No. NM_003504) has been identified as up-regulated in cancers, examples of which include, but are not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer. Thus, CDC45L is a candidate for the target of cancer/tumor immunotherapy.

The present invention further relates to the identification of specific epitope peptides of the gene products of CDC45L that possess the ability to induce CTLs specific to CDC45L. As discussed in detail below, peripheral blood mononuclear cells (PBMCs) obtained from a healthy donor were stimulated using HLA-A*2402 or HLA-A*0201 binding candidate peptides derived from CDC45L. CTL lines were then established with specific cytotoxicity against the HLA-A24 or HLA-A2 positive target cells pulsed with each of candidate peptides. These results demonstrate that these peptides are HLA-A24 or HLA-A2 restricted epitope peptides that may induce potent and specific immune responses against cells expressing CDC45L. Further, the results indicate that CDC45L is strongly immunogenic and that the epitopes thereof are effective targets for cancer/tumor immunotherapy.

Accordingly, it is an object of the present invention to provide isolated peptides that bind to HLA antigen, particularly those derived from CDC45L (SEQ ID NO: 18) or an immunologically active fragments thereof. These peptides are expected to have CTL inducibility and, thus, can be used to induce CTL ex vivo or to be administered to a subject for inducing immune responses against cancers such as testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, colorectal cancer and the like. Preferred peptides are nonapeptides or decapeptides, and more preferably, those having an amino acid sequence selected from among SEQ ID NOs: 1 to 16. Of these, the peptides having an amino sequence selected from among SEQ ID NOs: 2, 3, 4, 7 and 12 showed strong CTL inducibility and thus are most preferred.

The peptides of the present invention encompass those wherein one, two or more amino acids are substituted deleted or added, so long as the resulting modified peptides retain the original CTL inducibility. The present invention also provides isolated polynucleotides encoding any one of the peptides of the present invention. These polynucleotides can be used to induce APCs with CTL inducibility and can be administered to a subject for inducing immune responses against cancers much like the present peptides.

When administered to a subject, the present peptides are preferably presented on the surface of APCs so as to induce CTLs targeting the respective peptides. Accordingly, it is a further object of the present invention to provide compositions or agents that induce CTL, such compositions or substances including one or more peptides or polynucleotides of the present invention. The present invention further contemplates compositions or agents including one or more peptides or polynucleotides of the present invention formulated for the treatment and/or prophylaxis of cancers as well as the prevention of postoperative recurrence thereof, such cancers including, but not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer. Thus, the present invention also provides pharmaceutical compositions or agents for the treatment and/or prophylaxis of cancers, and/or the prevention of postoperative recurrence thereof, such pharmaceutical compositions or agents including one or more of the peptides or polynucleotides of the present invention. In addition to and/or instead of the aforementioned peptide or polynucleotide, the pharmaceutical compositions or agents of the present invention may optionally include as active ingredients APCs or exosomes that present one or more of the present peptides of the present invention.

The peptides and polynucleotides of the present invention can induce APCs that present on their surface a complex of an HLA antigen and a present peptide, for example, by contacting APCs derived from a subject with a peptide of the present invention or by introducing a polynucleotide encoding such a peptide into APCs. Such APCs have high CTL inducibility against target peptides and find use in cancer immunotherapy. Therefore, the present invention encompasses the methods for inducing APCs with CTL inducibility and the APCs obtained by such methods.

The present invention also provides a method for inducing CTL that includes the step of co-culturing CD8 positive cells with APCs or exosomes presenting a peptide of the present invention on its surface. Alternatively, the method may include the step of introducing a gene that includes a polynucleotide coding for a T cell receptor (TCR) subunit polypeptide capable of binding to a peptide of the present invention. The CTLs obtained by such methods can find use in the treatment and/or prevention of cancers, examples of which include, but are not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer. Therefore, the present invention encompasses the CTLs obtained by the present methods.

It is yet another object of the present invention to provide methods for inducing an immune response against cancer in a subject in need thereof, such methods including the step of administering compositions or agents including the CDC45L polypeptides of the present invention or an immunologically active fragment thereof, polynucleotides encoding the CDC45L polypeptides of the present invention, or exosomes or the APCs presenting such CDC45L polypeptides.

Specifically, the present invention provides the following [1] to [22];

[1] An isolated peptide binding to an HLA antigen and having cytotoxic T lymphocytes (CTL) inducibility, wherein the peptide is derived from a polypeptide consisting of the amino acid sequence of SEQ ID NO: 18 or an immunologically active fragment thereof,

[2] The isolated peptide of [1], wherein the HLA antigen is HLA-A24 or A2,

[3] The isolated peptide of [1] or [2], wherein said peptide comprises an amino acid sequence selected from the group consisting of:
 (a) SEQ ID NOs: 4, 2, 3, 7 and 12; and
 (b) SEQ ID NOs: 4, 2, 3, 7 and 12, wherein 1, 2, or several amino acids are substituted, inserted, deleted and/or added,

[4] The isolated peptide of any one of [1] to [3], wherein the peptide has one or both of the following characteristics:
 (a) the second amino acid from N-terminus is or is modified to be an amino acid selected from the group consisting of phenylalanine, tyrosine, methionine and tryptophan; and
 (b) the C-terminal amino acid is or is modified to be an amino acid selected from the group consisting of phenylalanine, leucine, isoleucine, tryptophan and methionine,

[5] The isolated peptide of any one of [1] to [3], wherein the peptide has one or both of the following characteristics:
 (a) the second amino acid from the N-terminus is or is modified to be an amino acid selected from the group consisting of leucine and methionine; and (b) the C-terminal amino acid is or is modified to be an amino acid selected from the group consisting of valine and leucine,

[6] The isolated peptide of any one of [1] to [5], wherein the peptide is nonapeptide or decapeptide,

[7] An isolated polynucleotide encoding the peptide of any one of [1] to [6],

[8] A composition for inducing CTL, wherein the composition comprises one or more of the peptide(s) set forth in any one of [1] to [6], or one or more of the polynucleotide(s) set forth in [7],

[9] A pharmaceutical composition for the treatment and/or prophylaxis of cancers, and/or the prevention of the postoperative recurrence thereof, wherein the composition comprises one or more of the peptide(s) set forth in any one of [1] to [6], or one or more of the polynucleotide(s) of [7],

[10] The pharmaceutical composition of [9] formulated for the administration to a subject whose HLA antigen is HLA-A24 or HLA-A2,

[11] The pharmaceutical composition of [9] or [10] formulated for the treatment of cancer,

[12] A method for inducing an antigen-presenting cell (APC) with CTL inducibility comprising a step selected from the group consisting of:

(a) contacting an APC with the peptide of any one of [1] to [6] in vitro, ex vivo or in vivo, and (b) introducing a polynucleotide encoding the peptide of any one of [1] to [6] into an APC,

[13] A method for inducing CTL, wherein the method comprises a step selected from the group consisting of:

(a) co-culturing CD8 positive T cells with APCs, which presents on its surface a complex of an HLA antigen and the peptide of any one of [1] to [6];

(b) co-culturing CD8 positive T cells with exosomes, which presents on its surface a complex of an HLA antigen and a peptide of any one of [1] to [6]; and (c) introducing a gene that comprises a polynucleotide encoding a T cell receptor (TCR) subunit polypeptide capable of binding to the peptide of any one of [1] to [6] into a T cell,

[14] An isolated APC that presents on its surface a complex of an HLA antigen and the peptide of any one of [1] to [6],

[15] The APC of [14], which is induced by the method of [12],

[16] An isolated CTL that targets any of the peptides of [1] to [6],

[17] The CTL of [16], which is induced by the method of [13],

[18] A method of inducing an immune response against cancer in a subject, wherein the method comprises administering to the subject a composition comprising one or more peptide(s) of [1] to [6], one or more immunologically active fragment(s) thereof, or one or more polynucleotide(s) encoding the peptide or the fragment,

[19] An antibody or fragment thereof against any of the peptides of [1] to [6],

[20] A vector comprising a nucleotide sequence encoding any of the peptides of [1] to [6],

[21] A host cell transformed or transfected with an expression vector according to [20], and

[22] A diagnostic kit comprising any of the peptides of [1] to [6], the nucleotide of [7] or the antibody of [19].

The applicability of the present invention extends to any of a number diseases relating to or arising from CDC45L overexpression, such as cancer, examples of which include, but are not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer.

In addition to the above, other objects and features of the invention will become more fully apparent when the following detailed description is read in conjunction with the accompanying figures and examples. However, it is to be understood that both the foregoing summary of the present invention and the following detailed description are of exemplified embodiments, and not restrictive of the present invention or other alternate embodiments of the present invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments that follows.

[FIG. 1a-d]FIG. 1 is composed of a series of photographs, A to F, depicting the results of CDC45L mRNA analyses expressed in human normal tissues, cancer cell lines and cancer tissues. Parts A, B: RT-PCR and Northern blot analysis of CDC45L mRNA expressed in various normal tissues. Part C: RT-PCR analysis of CDC45L mRNA expressed in various cancer cell lines. Part D: RT-PCR analysis of CDC45L mRNA expressed in lung cancer tissues and adjacent normal lung tissues.

[FIG. 1e-f]Part E: RT-PCR analysis of CDC45L mRNA expressed in various cancer cell lines derived from gastric, hepatobiliary, breast, pancreas and colorectal cancers. Part F: Immunohistochemical analysis of CDC45L protein expressed in adenocarcinoma, squamous carcinoma, small cell carcinoma, normal lung, testis and normal skin (original magnification X400). Positive staining signals are seen as brown. Scale bars, 50 micro-m.

FIG. 2 depicts a protocol for the induction of CDC45L-specific CTLs from PBMC. PBMCs were isolated from donors, and CD8$^+$ T cells and CD14$^+$ cells were isolated using anti-CD8 mAb- or anti-CD14 mAb-coated microbeads respectively from the PBMC of the HLA-A24 positive healthy donors and lung cancer patients. DCs were obtained from CD14$^+$ cells, trough culture in the presence of GM-CSF and IL-4 for 5 days. DCs were pulsed with HLA-A24 binding peptides in the presence of beta 2-microglobulin for 2 hrs at 37 degrees C. These peptide-pulsed DC were then irradiated and mixed at 1:20 ratio with autologous CD8$^+$ T cells to generate peptides-reactive CTLs. Cells were cultured with IL-7 in AIM-V supplemented with 2% auto serum on day 0 and these cultures were supplemented with IL-2 on day 2. Two additional weekly stimulations with peptide-loaded autologous PHA-blasts were carried out on day 7 and 14. INF-gamma ELISPOT, CD107a mobilization and $^{51}$Cr release assays were performed at 6 days after the third round of peptide stimulation of CD8+ T cells.

[FIG. 3]FIG. 3 is composed of a series of bar graphs, A to C, depicting the CTL response to CDC45L derived peptides in healthy donors. Parts A, B, C: ELISPOT assay of CDC45L peptide-reactive CTLs generated from the PBMCs of HLA-A24 positive healthy donors (A, C, healthy donor-1; B, healthy donor-4). CD8+ T cells were stimulated with autologous monocyte-derived DCs (day 0) and autologous PHA-blasts (days 7 and 14) pulsed with a mixture of 4 of 16 candidate peptides (SEQ ID NOs: 1 to 16). CTLs were collected on day 20, and the IFN-gamma-producing CTLs were detected by ELISPOT assay. Bars indicate number of IFN-gamma spots when the CTL lines were re-stimulated with C1R-A2402 cells pulsed with CDC45L derived peptides (open bars) or irrelevant HIV-A24 peptides (closed bars). The effector-to-target cell ratio is 10:1. Data are indicated as the mean+/−SD of triplicate assays. A representative of two independent experiments with similar results is shown for each donor.

FIG. 4 is composed of a series of panels depicting the level of CD107a exposed on the cell surface of CD8+ T cells after antigen stimulation. All peptides were used at a final concentration of 1 micro-g/ml. Events shown are gated for CD8+ T cells. Upper and middle panels: stimulated with the cognate CDC45L derived peptides. Lower panels: stimulated with the irrelevant HIV-A24 peptide. The numbers inside the plots indicate the percentage of the cell population with the quadrant characteristic (CD8+ CD107a+ T lymphocytes). Each lane is a representative of two independent experiments with similar results.

[FIG. 5a-c]FIG. 5 is composed of a series of graphs A to D, depicting the induction of CDC45L-specific human CTLs from PBMCs of the HLA-A24-positive lung cancer patients. Part A: ELISPOT assay of CTLs induced from the lung cancer patients co-cultured with target cells pulsed with CDC45L-A24-9-109-2 (SEQ ID NO: 2), CDC45L-A24-9-294-3 (SEQ ID NO: 3), CDC45L-A24-9-556-4 (SEQ ID NO: 4), CDC45L-A24-9-370-7 (SEQ ID NO: 7) or CDC45L-A24-10-556-12 (SEQ ID NO: 12) peptide The IFN-gamma production stimulated with peptide-pulsed C1R-A*2402 cells was significantly greater than that stimulated with HIV peptide-pulsed C1R-A*2402 cells. Bars indicate the number of IFN-gamma spots when the generated CTL lines were re-stimulated with C1R-A2402 cells pulsed with CDC45L derived peptides (open bars) or irrelevant HIV-A24 peptides (closed bars). The effector-to-target cell ratio was 10:1. Data are presented as the mean+/−SD of triplicate assays. Part B: Cytotoxicity of CTLs against C1R-A2402 cells pulsed with the cognate CDC45L derived peptides (white triangle; CDC45L-A24-9-109-2 (SEQ ID NO: 2), CDC45L-A24-9-294-3 (SEQ ID NO: 3), CDC45L-A24-9-556-4 (SEQ ID NO: 4), CDC45L-A24-9-370-7 (SEQ ID NO: 7) or CDC45L-A24-10-556-12 (SEQ ID NO: 12)) and C1R-A2402 cells pulsed with irrelevant HIV-A24 peptides (black triangle) in $^{51}$Cr-release assay. Each value represents the percentage of specific lysis calculated based on the mean values of a triplicate assay. Part C: Western blot analysis of whole cell lysates derived from Lu99 cells (left panel, lane 1), Lu99 cells transfected with CDC45L siRNA (left panel, lane 2) or control GFP siRNA (left panel, lane 3) and EBC-1 cells (right panel, lane 1), EBC-1 cells transfected with CDC45L siRNA (right panel, lane 2) or control GFP siRNA (right panel, Lane 3) using anti-CDC45L antibody. Beta-actin served as the internal control.

[FIG. 5d]Part D: Abrogation of CDC45L-specific cytotoxic activity of CTLs by down-regulation of CDC45L protein in Lu99 and EBC-1 target cells (CDC45L+, HLA-A*2402+). Cytotoxic activities of CTLs against Lu99, EBC-1, CDC45L siRNA Lu99, CDC45L siRNA EBC-1, GFP siRNA Lu99, GFP siRNA EBC-1, or A549 were analyzed by 51Cr-release assay. Each value represents the percentage of specific lysis calculated based on the mean values of a triplicate assay.

[FIG. 6]FIG. 6 is composed of a series of graphs depicting the inhibition of CDC45L reactive CTL responses by anti-HLA class I mAb. After the Lu99-target cells were incubated with anti-HLA class I mAb (W6/32, IgG2a) or control anti-HLA class II mAb (IgG2a) for 1 h, Lu99 cells were co-cultured with the CTLs generated from CD8+ T cells of healthy donors or lung cancer patients by stimulation with CDC45L-A24-9-109-2 (SEQ ID NO: 2), CDC45L-A24-9-294-3 (SEQ ID NO: 3), CDC45L-A24-9-556-4 (SEQ ID NO: 4) or CDC45L-A24-9-370-7 (SEQ ID NO: 7) peptide. IFN-gamma production (Part A) and cytotoxicity (Part B) mediated by CTLs is indicated. White circle, Lu99; Black circle, Lu99+W6/32; White box, Lu99+Control mAb. Data are presented as the mean+/−SD of triplicate assays. Statistically significant differences are indicated with asterisks (*P<0.05).

FIG. 7 is composed of a series of graphs, A to C, depicting the induction of both HLA-A24 (A*2402) and HLA-A2 (A*0201) restricted CTLs by stimulation with CDC45L-A2-9-556-4 (also referred herein as CDC45L-A24-9-556-4), $^{556}$KFLDALISL$^{564}$ (SEQ ID NO:4), peptide. Part A: IFN-gamma ELISPOT assay of CTLs induced from an HLA-A*0201 positive healthy donor co-cultured with T2 cells pulsed with CDC45L-A2-9-556-4 (SEQ ID NO: 4) peptide. Data are presented as the mean +/−SD of triplicate assays. Part B: Cytotoxic activity of CTLs against T2 cells pulsed with CDC45L-A2-9-556-4 (SEQ ID NO:4) peptide (white triangle), T2 cells pulsed with control HIV-A2 peptide (black triangle), and C1R-A2402 cells pulsed with CDC45L-A2-9-556-4 (SEQ ID NO: 4) peptide (black box) as analyzed by $^{51}$Cr-release assay. Part C: Inhibition of CDC45L-reactive CTL responses by anti-HLA class I mAb as analyzed by $^{51}$Cr-release assay. After the Panc1-target cells (CDC45L+, HLA-A2+, HLA-A24-) were incubated with anti-HLA class I mAb (W6/32, IgG2a) or control anti-HLA class II mAb (IgG2a), for 1 h, Panc1 cells were co-cultured with the CTLs generated from CD8+T cells of an HLA-A*0201 positive healthy donor by stimulation with CDC45L-A2-9-556-4 (SEQ ID NO: 4) peptide. White circle, Panel cells; Black circle, Panc1 +W6/32; White box, Panc1+Control mAb. Each value represents the percentage of specific lysis calculated based on the mean values of a triplicate assay. Representative data from three independent experiments with similar results is shown.

[FIG. 8a-b]FIG. 8 is composed of a series of graphs, A to D, depicting the in vivo antitumor activity of CDC45L-reactive human CTLs in NOD/SCID mice. Parts A, B, C: Peptide-specific cytotoxic activity of human CTLs generated from two healthy donors by stimulation with the mixture of three CDC45L derived peptides. Part A: IFN-gamma ELISPOT assay of CTLs co-cultured with C1R-A2402 cells pulsed with either CDC45L-A24-9-109-2 (SEQ ID NO: 2), CDC45L-A24-9-294-3 (SEQ ID NO: 3) or CDC45L-A24-9-556-4 (SEQ ID NO: 4) peptide. Part B: CDC45L specific cytotoxicity of CTLs against Lu99 (CDC45L+, HLA-A24+) in the absence (white circle) or presence of anti-HLA class I mAb (W6/32, black circle) or control anti-HLA class II mAb (white box) as analyzed by $^{51}$Cr-release assay.

[FIG. 8c-d]Part C: Cytotoxic activity of CTLs to C1R-A2402 cells pulsed with one of three CDC45L derived peptides (white circle, CDC45L-A24-9-109-2 (SEQ ID NO: 2);

Figure 2:
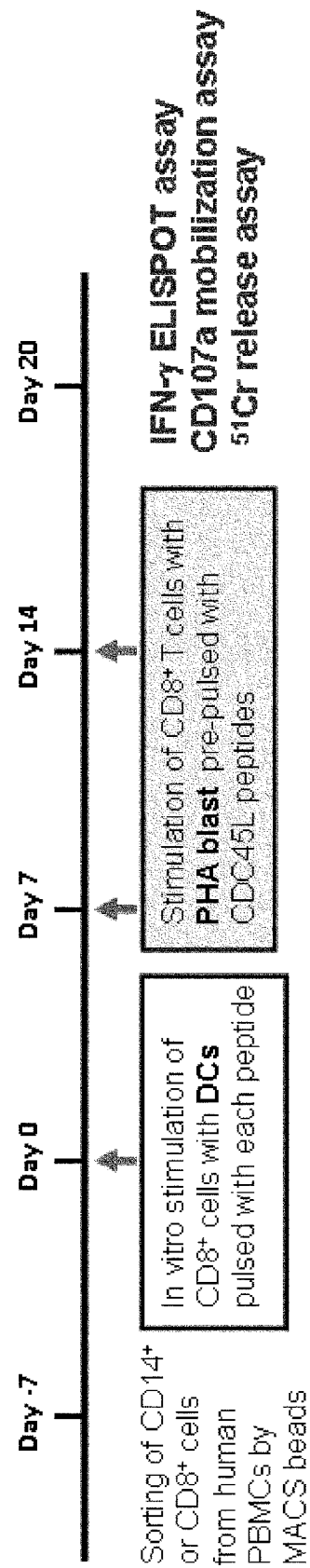
[FIG. 2]

white box, CDC45L-A24-9-294-3 (SEQ ID NO: 3); white triangle, CDC45L-A24-9-556-4 (SEQ ID NO: 4)) or an irrelevant HIV-A24 peptide (black circle) as analyzed by $^{51}$Cr-release assay. Part D: Tumors in NOD/SCID mice inoculated intravenously with CDC45L-induced CTLs (black box, n=5), control CD8$^+$ T cells (white lozenge, n=5), or PBS alone (white circle, n=5). When the tumor size reached approximately 25 mm$^2$ on day 7 after subcutaneously tumor implantation, human CTLs (4×10$^6$) reactive to a mixture of three CDC45L peptides were inoculated intravenously. The CTL inoculation was repeated on day 14. The control CD8$^+$ T cells stimulated with an irrelevant HLA-A24 restricted HIV peptide were also inoculated into mice as a control. The tumor size is expressed in square millimeters. Each symbol represents mean tumor sizes in each group of mice; bars indicate SD. Two-tailed Student's t-test was used to determine the significance of differences between the two groups on day 42.

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and/or optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

I. Definitions

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "amino acid" as used herein refers to naturally occurring and synthetic amino acids, as well as amino acid analogs and amino acid mimetics that similarly function to the naturally occurring amino acids. Amino acid may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have one or more modified R group(s) or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated are referred to by their commonly accepted single-letter codes.

The term "composition" as used herein is intended to encompass a product including the specified ingredients in the specified amounts, as well as any product that results, directly or indirectly, from combination of the specified ingredients in the specified amounts. Such term in relation to "pharmaceutical composition", is intended to encompass a product including the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the phrase "pharmaceutical composition" encompasses any composition made by admixing a compound of the present invention and a pharmaceutically or physiologically acceptable carrier. The phrase "pharmaceutically acceptable carrier" or "physiologically acceptable carrier", as used herein, means a pharmaceutically or physiologically acceptable material, composition, substance or vehicle, including but not limited to, a liquid or solid filler, diluent, excipient, solvent or encapsulating material, involved in carrying or transporting the active ingredient(s) from one organ, or portion of the body, to another organ, or portion of the body.

Unless otherwise defined, the term "cancer" refers to the cancers or tumors that overexpress the CDC45L gene, examples of which include, but are not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the terms "HLA-A24" refers to the HLA-A24 type containing the subtypes such as HLA-A*2402.

Unless otherwise defined, the term "HLA-A2", as used herein, representatively refers to the subtypes such as HLA-A*0201 and HLA-A*0206.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

To the extent that the methods and compositions of the present invention find utility in the context of the "treatment" of cancer, a treatment is deemed "efficacious" if it leads to clinical benefit such as, reduction in expression of CDC45L gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM.

Unless otherwise defined, all technical and scientific terms used herein have the same meaning as commonly understood by one of ordinary skill in the art to which the present invention belongs.

II. Peptides

To demonstrate that peptides derived from CDC45L function as an antigen recognized by CTLs, peptides derived from CDC45L (SEQ ID NO: 18) were analyzed to determine whether they were antigen epitopes restricted by HLA-A24 or A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A24 binding peptides derived from CDC45L were identified based on their binding affinities to HLA-A24. The following peptides are considered to be candidate peptides for immunotherapy;

CDC45L-A24-9-237-1 (SEQ ID NO: 1),
CDC45L-A24-9-109-2 (SEQ ID NO: 2),
CDC45L-A24-9-294-3 (SEQ ID NO: 3),
CDC45L-A24-9-556-4 (SEQ ID NO: 4),
CDC45L-A24-9-328-5 (SEQ ID NO: 5),
CDC45L-A24-9-396-6 (SEQ ID NO: 6),
CDC45L-A24-9-370-7 (SEQ ID NO: 7),
CDC45L-A24-9-192-8 (SEQ ID NO: 8),
CDC45L-A24-9-541-9 (SEQ ID NO: 9),
CDC45L-A24-9-364-10 (SEQ ID NO: 10),
CDC45L-A24-10-109-11 (SEQ ID NO: 11),
CDC45L-A24-10-556-12 (SEQ ID NO: 12),
CDC45L-A24-10-271-13 (SEQ ID NO: 13),
CDC45L-A24-10-313-14 (SEQ ID NO: 14),
CDC45L-A24-10-21-15 (SEQ ID NO: 15), and
CDC45L-A24-10-459-16 (SEQ ID NO: 16).

Moreover, after in vitro stimulation of T-cells by dendritic cells (DCs) pulsed (loaded) with these peptides, CTLs were successfully established using each of the following peptides;

CDC45L-A24-9-109-2 (SEQ ID NO: 2),
CDC45L-A24-9-294-3 (SEQ ID NO: 3),
CDC45L-A24-9-556-4 (SEQ ID NO: 4),
CDC45L-A24-9-370-7 (SEQ ID NO: 7), and
CDC45L-A24-10-556-12 (SEQ ID NO: 12).

These established CTLs showed potent specific CTL activity against target cells pulsed with respective peptides. The results herein demonstrate that CDC45L is an antigen recognized by CTLs and that the peptides tested are epitope peptides of CDC45L restricted by HLA-A24.

Among these peptides, CDC45L-A24-9-556-4 (SEQ ID NO: 4) was also identified as candidate of HLA-A2 binding peptide. Herein, CDC45L-A24-556-4 (SEQ ID NO: 4) is also referred to as CDC45L-A2-9-556-4 (SEQ ID NO: 4) in the context of the HLA-A2 restricted peptides. Using the peptide, CTLs against target cells that express CDC45L and HLA-A2 were successfully established. Thus, CDC45L-A2-9-556-4 (SEQ ID NO: 4) is not only an epitope peptide restricted by HLA-A24, but also an epitope peptide restricted by HLA-A24.

Since the CDC45L gene is over expressed in cancer cells and tissue, including for example those of testicular tumor, pancreatic cancer, bladder cancer, non-small cell lung cancer, small cell lung cancer, breast cancer, and esophageal cancer, prostate cancer, chronic myeloid leukemia (CML), soft tissue tumor, gastric cancer, hepatobiliary cancer, and colorectal cancer and not expressed in most normal organs, it represents a good target for cancer immunotherapy. Thus, the present invention provides nonapeptides (peptides consisting of nine amino acid residues) and decapeptides (peptides consisting of ten amino acid residues) corresponding to CTL-recognized epitopes from CDC45L. Alternatively, the present invention provides isolated peptides that bind to HLA antigens and induce cytotoxic T lymphocytes (CTLs), wherein the peptide has the amino acid sequence of SEQ ID NO: 18 or is an immunologically active fragment thereof. Particularly preferred examples of the present invention include those peptides having an SEQ ID NOs: 2, 3, 4, 7 and 12.

Generally, software programs presently available, for example, on the Internet, such as those described in Parker K C et al., J Immunol 1994 Jan. 1, 152(1): 163-75 and Nielsen M et al., Protein Sci 2003; 12: 1007-17 can be used to calculate the binding affinities between various peptides and HLA antigens in silico. Binding affinity with HLA antigens can be measured as described, for example, in Parker K C et al., J Immunol 1994 Jan. 1, 152(1): 163-75, Kuzushima K et al., Blood 2001, 98(6): 1872-81, Larsen M V et al. BMC Bioinformatics. 2007 Oct. 31; 8: 424, Buus S et al. Tissue Antigens., 62:378-84, 2003, Nielsen M et al., Protein Sci 2003; 12: 1007-17, and Nielsen M et al. PLoS ONE 2007; 2: e796, which are summarized in, e.g., Lafuente E M et al., Current Pharmaceutical Design, 2009, 15, 3209-3220. The methods for determining binding affinity is described, for example, in the Journal of Immunological Methods, 1995, 185: 181-190 and Protein Science, 2000, 9: 1838-1846. Therefore, one can select fragments derived from CDC45L that have high binding affinity with HLA antigens using such software programs. Thus, the present invention encompasses peptides composed of any fragments derived from CDC45L that bind with HLA antigens by such known programs. Furthermore, such peptides may include the peptide consisting of the full length of CDC45L.

The nonapeptides and decapeptides of the present invention may be flanked with additional amino acid residues, so long as the resulting peptide retains its CTL inducibility. The additional amino acid residues may be composed of any kind of amino acids so long as they do not impair the CTL inducibility of the original peptide. Thus, the present invention encompasses peptides with binding affinity to HLA antigens, including peptides derived from CDC45L. Such peptides are, for example, less than about 40 amino acids, often less than about 20 amino acids, and usually less than about 15 amino acids.

In general, the modification of one or more amino acids in a peptide will not influence the function of the peptide, and in some cases will even enhance the desired function of the original protein. In fact, modified peptides (i.e., peptides composed of an amino acid sequence in which one, two or several amino acid residues have been modified (i.e., substituted, added, deletedm and/or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention have both CTL inducibility and an amino acid sequence selected from among SEQ ID NOs: 2, 3, 4, 7 and 12, wherein one, two or even more amino acids are added, deleted and/or substituted.

Those of skill in the art will recognize that individual additions deletions or substitutions to an amino acid sequence that alter a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of amino acid side chain characteristics that are desirable to conserve include, for example: hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic group containing side-chain (H, F, Y, W). In addition, the following eight groups each contain amino acids that are accepted in the art as conservative substitutions for one another:
1) Alanine (A), Glycine (G);
2) Aspartic acid (D), Glutamic acid (E);
3) Aspargine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and may include non-conservative modifications, so long as the modified peptide retains the CTL inducibility of the original peptide. Furthermore, modified peptides should not exclude CTL inducible peptides of polymorphic variants, interspecies homologues, and alleles of CDC45L.

To retain the requisite CTL inducibility one can modify (i.e., insert, delete, add and/or substitute) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably 15% or less, and even more preferably 10% or less or 1 to 5%.

When used in the context of cancer immunotherapy, the peptides of the present invention should be presented on the surface of a cell or exosome, preferably as a complex with an HLA antigen. Therefore, it is preferable to select peptides that not only induce CTLs but also possess high binding affinity to the HLA antigen. To that end, the peptides can be modified by substitution, insertion, and/or addition of the amino acid residues to yield a modified peptide having improved binding affinity. In addition to peptides that are naturally displayed, since the regularity of the sequences of peptides displayed by binding to HLA antigens has already been known (J Immunol 1994, 152: 3913; Immunogenetics 1995, 41: 178; J Immunol 1994, 155: 4307), modifications based on such regularity may be introduced into the immunogenic peptides of the present invention.

For example, it may be desirable to substitute the second amino acid from the N-terminus with phenylalanine, tyrosine, methionine, or tryptophan, and/or the amino acid at the C-terminus with phenylalanine, leucine, isoleucine, tryptophan, or methionine in order to increase the HLA-A24 binding affinity. Thus, peptides having an amino acid sequence selected from among SEQ ID NOs: 2, 3, 4, 7 and 12, wherein the second amino acid from the N-terminus is substituted with phenylalanine, tyrosine, methionine, or tryptophan, and/or wherein the C-terminus is substituted with phenylalanine, leucine, isoleucine, tryptophan, or methionine are encompassed by the present invention.

Alternatively, it may be desirable to substitute the second amino acid from the N-terminus with leucine or methionine, and/or the amino acid at the C-terminus with valine or leucine in order to increase the HLA-A2 binding affinity. Thus, peptides having an amino acid sequence selected from among SEQ ID NO: 4 wherein the second amino acid from the N-terminus is substituted with leucine or methionine, and/or wherein the C-terminus is substituted with valine or leucine are encompassed by the present invention.

Substitutions may be introduced not only at the terminal amino acids but also at the position of potential T cell receptor (TCR) recognition of peptides. Several studies have demonstrated that a peptide with amino acid substitutions may have equal to or better function than that of the original, for example, CAP1, p53$_{(264-272)}$, Her-2/neu$_{(369-377)}$ or gp100$_{(209-217)}$ (Zaremba et al. Cancer Res. 57, 4570-4577, 1997, T. K. Hoffmann et al. J. Immunol. (2002) February 1; 168(3):1338-47., S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids may also be added to the N and/or C-terminus of the present peptides. Such modified peptides having high HLA antigen binding affinity and retained CTL inducibility are also included in the present invention.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide may be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce cytotoxic lymphocytes (CTLs) when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8 positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependent on MHC(HLA) class II restricted T(H) response) can be used. For example, the target cells may be radiolabeled with $^{51}$Cr and such, and cytotoxic activity may be calculated from radioactivity released from the target cells. Alternatively, CTL inducibility can be assessed may be examined by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, it was discovered that nonapeptides or decapeptides selected from among SEQ ID NOs: 2, 3, 4, 7 and 12 showed particularly high CTL inducibility as well as high binding affinity to an HLA antigen. Thus, these peptides are exemplified as preferred embodiments of the present invention.

Furthermore, the result of homology analysis showed that those peptides do not have significant homology with peptides derived from any other known human gene products. Accordingly, the possibility of unknown or undesired immune responses when used for immunotherapy is lowered. Therefore, also from this aspect, these peptides find use for eliciting immunity in cancer patients against CDC45L. Thus, the peptides of the present invention, preferably, peptides having an amino acid sequence selected from among SEQ ID NOs: 2, 3, 4, 7 and 12.

In addition to the above-described modifications, the peptides of the present invention may also be linked to other peptides, so long as the resulting linked peptide retains the requisite CTL inducibility of the original peptide. Examples of suitable peptides include: the peptides of the present invention or the CTL inducible peptides derived from other TAAs. Suitable inter-peptide linkers are well known in the art and include, for example, AAY (P. M. Daftarian et al., J Trans Med 2007, 5:26), AAA, NKRK (R. P. M. Sutmuller et al., J. Immunol. 2000, 165: 7308-7315) or K (S. Ota et al., Can Res. 62, 1471-1476, K. S. Kawamura et al., J. Immunol. 2002, 168: 5709-5715).

For example, non-CDC45L tumor associated antigen peptides also can be used substantially simultaneously to increase the immune response via HLA class I and/or class II. It is well established that cancer cells can express more than one tumor associated gene. Thus, it is within the scope of routine experimentation for one of ordinary skill in the art to determine whether a particular subject expresses additional tumor associated genes, and then to include HLA class I and/or HLA class II binding peptides derived from expression products of such genes in CDC45L compositions or vaccines according to the present invention.

Examples of HLA class I and HLA class II binding peptides are known to those of ordinary skill in the art (for example, see Coulie, Stem Cells 13:393-403, 1995), and can be used in the invention in a like manner as those disclosed herein. Thus, one of ordinary skill in the art can readily prepare polypeptides including one or more CDC45L peptides and one or more of the non-CDC45L peptides, or nucleic acids encoding such polypeptides, using standard procedures of molecular biology.

The above such linked peptides are referred to herein as "polytopes", i.e., groups of two or more potentially immunogenic or immune response stimulating peptides which can be joined together in various arrangements (e.g., concatenated, overlapping). The polytope (or nucleic acid encoding the polytope) can be administered in a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci. USA 92(13):5845-5849, 1995; Gilbert et al., Nature Biotechnol. 15(12):1280-1284, 1997; Thomson et al., J. Immunol. 157(2):822-826, 1996; Tarn et al., J. Exp. Med. 171(1):299-306, 1990). Polytopes containing various numbers and combinations of epitopes can be prepared and tested for recognition by CTLs and for efficacy in increasing an immune response.

The peptides of the present invention may also be linked to other substances, so long as the resulting linked peptide retains the requisite CTL inducibility of the original peptide. Examples of suitable include, for example: peptides, lipids, sugar and sugar chains, acetyl groups, natural and synthetic polymers, etc. The peptides may contain modifications such as glycosylation, side chain oxidation, or phosphorylation, etc., provided the modifications do not destroy the biological activity of the original peptide. These kinds of modifications may be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept may also be adapted to the present polypeptides. The stability of a polypeptide may be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, deleted and/or added by one, two or several amino acid residues, those having same or higher activity as compared to original peptides can be screened for or selected. The present invention, therefore, also provides the method of screening for or selecting modified peptides having same or higher activity as compared to originals. An illustrative method may include steps of:

a: substituting, deleting or adding at least one amino acid residue of a peptide of the present invention, b: determining the activity of the peptide produced in the step (a), and c: selecting the peptide having same or higher activity as compared to the original.

Herein, the activity to be assayed may include MHC binding activity, APC or CTL inducibility and cytotoxic activity. Preferably, the activity to be assayed is CTL inducibility and such activity can be assayed using the methods described in "EXAMPLES"

Herein, the peptides of the present invention may also be described as "CDC45L peptide(s)" or "CDC45L polypeptide(s)".

III. Preparation of CDC45L Peptides

The peptides of the present invention may be prepared using well known techniques. For example, the peptides may be prepared synthetically, using recombinant DNA technology or chemical synthesis. The peptides of the present invention may be synthesized individually or as longer polypeptides including two or more peptides. The peptides may then be isolated, i.e., purified or isolated so as to be substantially free from other naturally occurring host cell proteins and fragments thereof, or any other chemical substances.

The peptides of the present invention may contain modifications, such as glycosylation, side chain oxidation, or phosphorylation, provided the modifications do not destroy the biological activity of the original peptide. Other illustrative modifications include incorporation of D-amino acids or other amino acid mimetics that may be used, for example, to increase the serum half life of the peptides.

A peptide of the present invention may be obtained through chemical synthesis based on the selected amino acid sequence. Examples of conventional peptide synthesis methods that may be adapted for the synthesis include:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides may be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. Such vectors and host cells are also provided by the present invention. The host cell is then cultured to produce the peptide of interest. The peptide may also be produced in vitro adopting an in vitro translation system.

IV. Polynucleotides

The present invention also provides polynucleotides which encode any of the aforementioned peptides of the present invention. These include polynucleotides derived from the natural occurring CDC45L gene (GenBank Accession No. NM_003504 (for example, SEQ ID NO: 17)) as well as those having a conservatively modified nucleotide sequences thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon may be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of skill in the art will recognize that each codon in a nucleic acid (except AUG, which is ordinarily the only codon for methionine, and TGG, which is ordinarily the only codon for tryptophan) may be modified to yield a functionally identical molecule. Accordingly, each silent variation of a nucleic acid that encodes a peptide is implicitly described in each disclosed sequence.

The polynucleotide of the present invention may be composed of DNA, RNA, or derivatives thereof. As is well known in the art, a DNA molecule is composed of bases such as the naturally occurring bases A, T, C, and G, and T is replaced by U in an RNA. One of skill will recognize that non-naturally occurring bases be included in polynucleotides, as well.

The polynucleotide of the present invention may encode multiple peptides of the present invention with or without intervening amino acid sequences. For example, the intervening amino acid sequence may provide a cleavage site (e.g., enzyme recognition sequence) of the polynucleotide or the translated peptides. Furthermore, the polynucleotide may include any additional sequences to the coding sequence encoding the peptide of the present invention. For example, the polynucleotide may be a recombinant polynucleotide that includes regulatory sequences required for the expression of the peptide or may be an expression vector (plasmid) with marker genes and such. In general, such recombinant polynucleotides may be prepared by the manipulation of polynucleotides through conventional recombinant techniques using, for example, polymerases and endonucleases.

Both recombinant and chemical synthesis techniques may be used to produce the polynucleotides of the present invention. For example, a polynucleotide may be produced by insertion into an appropriate vector, which may be expressed when transfected into a competent cell. Alternatively, a polynucleotide may be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide may be synthesized using the solid phase techniques, as described in Beaucage S L & Iyer R P, Tetrahedron 1992, 48: 2223-311; Matthes et al., EMBO J. 1984, 3: 801-5.

V. Exosomes

The present invention further provides intracellular vesicles called exosomes, which present complexes formed between the peptides of the present invention and HLA antigens on their surface. Exosomes may be prepared, for example using the methods detailed in Japanese Patent Application Kohyo Publications No. Hei 11-510507 and WO99/03499, and may be prepared using APCs obtained from patients who are subject to treatment and/or prevention. The exosomes of the present invention may be inoculated as vaccines, in a fashion similar to the peptides of the present invention.

The type of HLA antigens included in the complexes must match that of the subject requiring treatment and/or prevention. For example, in the Japanese population, HLA-A24 and HLA-A2, particularly HLA-A*2402 and HLA-A*0201 and HLA-A*0206, are most prevalent and therefore would be appropriate for the treatment of a Japanese patient. The use of the A24 and A2 types that are highly expressed among the Japanese and Caucasian is favorable for obtaining effective results, and subtypes such as A*2402, A*0201 and A*0206 also find use. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, deletion, insertion ad/or addition of 1, 2, or several amino acids may be performed based on the amino acid sequence of the naturally occurring CDC45L partial peptide.

When using the A24 type HLA antigen for the exosome of the present invention, the peptides having an amino acid sequence selected from among SEQ ID NOs: 2, 3, 4, 7 and 12 find use.

Alternatively, when using the A2 type HLA antigen for the exosome of the present invention, peptide having the amino acid sequence of SEQ ID NO: 4 finds use.

VI. Antigen-Presenting Cells (APCS)

The present invention also provides isolated antigen-presenting cells (APCs) that present complexes formed with HLA antigens and the peptides of the present invention on its surface. The APCs may be derived from patients who are subject to treatment and/or prevention, and may be administered as vaccines by themselves or in combination with other drugs including the peptides of the present invention, exosomes, or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DC is a representative APC having the strongest CTL inducing activity among APCs, DCs find use as the APCs of the present invention.

For example, the APCs of the present invention may be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention are induced in the body of the subject. The phrase "inducing APC" includes contacting (stimulating) a cell with the peptides of the present invention, or nucleotides encoding peptides of the present invention to present complexes formed between HLA antigens and the peptides of the present invention on cell's surface. Therefore, the APCs of the present invention may be obtained by collecting the APCs from the subject after administering the peptides of the present invention to the subject. Alternatively, the APCs of the present invention may be obtained by contacting APCs collected from a subject with the peptide of the present invention.

The APCs of the present invention may be administered to a subject for inducing immune response against cancer in the subject by themselves or in combination with other drugs including the peptides, exosomes or CTLs of the present invention. For example, the ex vivo administration may include steps of:

a: collecting APCs from a first subject, b: contacting with the APCs of step a, with the peptide, and c: administering the APCs of step b to a second subject.

The first subject and the second subject may be the same individual, or may be different individuals. The APCs obtained by step b may be used as a vaccine for the treatment and/or prevention of cancer, examples of which include but are not limited to testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer.

The present invention provides for the manufacture of a pharmaceutical composition including such antigen-presenting cells induced with peptides of the present invention.

According to an aspect of the present invention, the APCs have a high level of CTL inducibility. In the term of "high level of CTL inducibility", the high level is relative to the level of that by APC contacting with no peptide or peptides which may not induce the CTL. Such APCs having a high level of CTL inducibility may be prepared by a method that includes the step of transferring a polynucleotide encoding the peptide of the present invention to APCs in vitro as well as the method mentioned above. The introduced genes may be in the form of DNAs or RNAs. Examples of methods for introduction include, without particular limitations, various methods conventionally performed in this field, such as lipofection, electroporation, or calcium phosphate method may be used. More specifically, it may be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present partial peptides.

In preferred embodiments, the APCs of the present invention may be those that present complexes formed between an HLA-A24 antigen such as HLA-A*2402 and the peptide of the present invention on its surface. Alternatively, the APCs of the present invention may present complexes formed between an HLA-A2 antigen such as HLA-A*0201 and the peptide of SEQ ID NO: 4 or the modified peptide thereof on its surface.

VII. Cytotoxic T Lymphocytes (CTLS)

A CTL induced against any one of the peptides of the present invention strengthens the immune response targeting cancer cells in vivo and thus may be used as vaccines, in a fashion similar to the peptides per se. Thus, the present invention provides isolated CTLs that are specifically induced or activated by any one of the present peptides.

Such CTLs may be obtained by (1) administering the peptide(s) of the present invention to a subject or (2) contacting (stimulating) subject-derived APCs, and CD8 positive cells, or peripheral blood mononuclear leukocytes in vitro with the peptide(s) of the present invention or (3) contacting CD8 positive cells or peripheral blood mononuclear leukocytes in vitro with the APCs or exosomes presenting a complex of an HLA antigen and the peptide on its surface or (4) introducing a gene that includes a polynucleotide encoding a T cell receptor (TCR) subunit capable of binding to the peptide of the present invention. Such APCs or exosomes may be prepared by the methods described above and details of the method of (4) is described bellow in section "VIII. T cell receptor (TCR)".

The CTLs of the present invention may be derived from patients who are subject to treatment and/or prevention, and may be administered by themselves or in combination with other drugs including the peptides of the present invention or exosomes for the purpose of regulating effects. The obtained CTLs act specifically against target cells presenting the peptides of the present invention, for example, the same peptides used for induction. The target cells may be cells that endogenously express CDC45L, such as cancer cells, or cells that are transfected with the CDC45L gene; and cells that present a peptide of the present invention on the cell surface due to stimulation by the peptide may also serve as targets of activated CTL attack.

VIII. T Cell Receptor (TCR)

The present invention also provides a composition including nucleic acids encoding polypeptides that are capable of forming a subunit of a T cell receptor (TCR), and methods of using the same. The TCR subunits of the present invention have the ability to form TCRs that confer specificity to T cells against tumor cells presenting CDC45L. By using the known methods in the art, the nucleic acids encoding alpha- and beta-chains that constitute the TCR subunits of the CTL induced with one or more peptides of the present invention may be identified (WO2007/032255 and Morgan et al., J Immunol, 171, 3288 (2003)). For example, the PCR methods are preferred to analyze the nucleotide sequences encoding TCR subunits. The PCR primers for the analysis can be, for example, 5'-R primers (5'-gtctaccaggcattcgcttcat-3') as 5' side primers (SEQ ID NO: 23) and 3-TRa-C primers (5'-tcagctg-gaccacagccgcagcgt-3') specific to TCR alpha chain C region (SEQ ID NO: 24), 3-TRb-C1 primers (5'-tcagaaatcctttctct-tgac-3') specific to TCR beta chain C1 region (SEQ ID NO: 25) or 3-TRbeta-C2 primers (5'-ctagcctctggaatcctttctctt-3') specific to TCR beta chain C2 region (SEQ ID NO: 26) as 3' side primers, but not limited thereto. The derivative TCRs may bind target cells displaying the CDC45L peptide with high avidity, and optionally mediate efficient killing of target cells presenting the CDC45L peptide in vivo and in vitro.

The nucleic acids encoding the TCR subunits may be incorporated into suitable vectors, e.g., retroviral vectors. These vectors are well known in the art. The nucleic acids or the vectors including them usefully may be transferred into a T cell, for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

The specific TCR is a receptor capable of specifically recognizing a complex of a peptide of the present invention and HLA molecule, giving a T cell specific activity against the target cell when the TCR is presented on the surface of the T cell. A specific recognition of the above complex may be confirmed by any known methods, preferred examples of which include, but are not limited to, HLA multimer staining analysis using HLA molecules and peptides of the present invention, and ELISPOT assay. By performing the ELISPOT assay, it can be confirmed whether a T cell transduced with the nucleic acid encoding the TCR subunits recognizes a cell expressing HLA molecule and CDC45L, and the signal is transmitted intracellularly. It can also be confirmed whether the TCR subunits introduced into a T cell can give a T cell cytotoxic activity by known methods in the art. Preferred methods include, for example, chromium release assay using HLA-A2 positive and CDC45L overexpressing cells as target cells.

Also, the present invention provides CTLs which are prepared by transduction with the nucleic acids encoding the TCR subunits polypeptides that bind to the CDC45L peptide of, e.g., SEQ ID NO: 4 in the context of HLA-A2, and also the peptides of SEQ ID NOs: 2, 3, 4, 7 and 12 in the context of HLA-A24. The transduced CTLs are capable of homing to cancer cells in vivo, and may be expanded by well known culturing methods in vitro (e.g., Kawakami et al., J. Immunol., 142, 3452-3461 (1989)). The CTLs of the present invention may be used to form an immunogenic composition useful in treating and/or the preventing of cancer in a patient in need of therapy or protection (See WO2006/031221 the contents of which are incorporated by reference herein).

IX. Pharmaceutical Agents or Compositions

Since CDC45L expression is specifically elevated in cancers, examples of which include but are not limited to testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer as compared with normal tissue, the peptides of the present invention and polynucleotides encoding such peptides find utility in the treatment and/or prophylaxis of cancer, and/or the prevention of postoperative recurrence thereof. Thus, the present invention provides a pharmaceutical agent or composition for treating and/or preventing cancer, and/or for preventing the postoperative recurrence thereof, such pharmaceutical agent or composition including as an active ingredient one or more of the peptides or polynucleotides of the present invention. Alternatively, the present peptides may be expressed on the surface of any of the foregoing exosomes or cells, such as APCs for the use as pharmaceutical s agent s or compositions. In addition, the aforementioned CTLs which target any one of the peptides of the present invention may also be used as the active ingredient of the present pharmaceutical agent s or compositions.

The pharmaceutical agent s and compositions (i.e., "pharmaceutical agents") of the present invention also find use as vaccines. In the context of the present invention, the phrase "vaccine" (also referred to as an "immunogenic composition") refers to a substance that has the function to induce anti-tumor immunity upon inoculation into animals.

The pharmaceutical agents or compositions of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

In another embodiment, the present invention also provides the use of an active ingredient selected from among:

(a) a peptide of the present invention;

(b) a nucleic acid encoding such a peptide as disclosed herein in an expressible form;

(c) an APC or an exosome presenting a peptide of the present invention on its surface; and (d) a cytotoxic T cell of the present invention in manufacturing a pharmaceutical composition or agent for treating or preventing cancer or tumor.

Alternatively, the present invention further provides an active ingredient selected from among:
(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention
for use in the treatment or prevention of cancer or tumor.

Alternatively, the present invention further provides a method or process for manufacturing a pharmaceutical composition or agent for treating or preventing cancer or tumor, wherein the method or process includes the step of formulating a pharmaceutically or physiologically acceptable carrier with an active ingredient selected from among:
(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention
as active ingredients.

In another embodiment, the present invention also provides a method or process for manufacturing a pharmaceutical composition or agent for treating or preventing cancer or tumor, wherein the method or process includes the steps of admixing an active ingredient with a pharmaceutically or physiologically acceptable carrier, wherein the active ingredient is selected from among:
(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention.

According to the present invention, peptides having the amino acid sequence of SEQ ID NO: 2, 3, 4, 7 and 12 have been found to be HLA-A24 restricted epitope peptides or the candidates that may induce potent and specific immune response. Therefore, the present pharmaceutical agents or compositions which include any of these peptides with the amino acid sequences of SEQ ID NOs: 2, 3, 4, 7 and 12 are particularly suited for the administration to subjects whose HLA antigen is HLA-A24. The peptide having the amino acid sequence of SEQ ID NO: 4 has been also found to be HLA-A2 restricted epitope peptides. Therefore, the pharmaceutical agents or compositions which include a peptide with amino acid sequence of SEQ ID NO: 4 are also suited for the administration to subjects whose HLA antigen is HLA-A2, in addition to subjects whose HLA antigen is HLA-A24. The same applies to pharmaceutical agents or compositions that contain polynucleotides encoding any of these peptides (i.e., the polynucleotides of the present invention).

Cancers to be treated by the pharmaceutical agents or compositions of the present invention are not limited and include any cancer in which CDC45L is involved (e.g., is overexpressed), including, for example, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer.

The present pharmaceutical agents or compositions may contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical agents or compositions of the present invention may optionally include other therapeutic substances as an active ingredient, so long as the substance does not inhibit the antitumoral effect of the active ingredient, e.g., any of the present peptides. For example, formulations may include anti-inflammatory agents or compositions, pain killers, chemotherapeutics, and the like. In addition to other therapeutic substances in the medicament itself, the medicaments of the present invention may also be administered sequentially or concurrently with the one or more other pharmacologic agents or compositions. The amounts of medicament and pharmacologic agent or composition depend, for example, on what type of pharmacologic agent(s) or composition(s) is/are used, the disease being treated, and the scheduling and routes of administration.

It should be understood that in addition to the ingredients particularly mentioned herein, the pharmaceutical agents or compositions of the present invention may include other agents or compositions conventional in the art having regard to the type of formulation in question.

In one embodiment of the present invention, the present pharmaceutical agents or compositions may be included in articles of manufacture and kits containing materials useful for treating the pathological conditions of the disease to be treated, e.g., cancer. The article of manufacture may include a container of any of the present pharmaceutical substances or compositions with a label. Suitable containers include bottles, vials, and test tubes. The containers may be formed from a variety of materials, such as glass or plastic. The label on the container should indicate the substance or composition is used for treating or prevention of one or more conditions of the disease. The label may also indicate directions for administration and so on.

In addition to the container described above, a kit including a pharmaceutical agent or composition of the present invention may optionally further include a second container housing a pharmaceutically-acceptable diluent. It may further include other materials desirable from a commercial and user standpoint, including other buffers, diluents, filters, needles, syringes, and package inserts with instructions for use.

The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptides of the present invention can be administered directly as a pharmaceutical agent or composition, or if necessary, formulated by conventional formulation methods. In the latter case, in addition to the peptides of the present invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of the present invention can be used for anticancer purposes.

The peptides of the present invention can be prepared as a combination composed of two or more of peptides of the present invention, to induce CTL in vivo. The peptide combination can take the form of a cocktail or can be conjugated to each other using standard techniques. For example, the peptides can be chemically linked or expressed as a single fusion polypeptide sequence that may have one or several amino acid(s) as a linker (e.g., Lysine linker: K. S. Kawamura et al. J. Immunol. 2002, 168: 5709-5715). The peptides in the combination can be the same or different. By administering the peptides of the present invention, the peptides are presented in high density by the HLA antigens on APCs, then CTLs that specifically react toward the complex formed between the displayed peptide and the HLA antigen are induced. Alternatively, APCs (e.g., DCs) are removed from subjects and then stimulated by the peptides of the present invention to obtain APCs that present any of the peptides of the present invention on their cell surface. These APCs are readministered to the subjects to induce CTLs in the subjects, and as a result, aggressiveness towards the tumor-associated endothelium can be increased.

The pharmaceutical agents or compositions for the treatment and/or prevention of cancer containing as an active ingredient a peptide of the present invention, can also include an adjuvant known to effectively establish cellular immunity. Alternatively, the pharmaceutical substances or composition can be administered with other active ingredients, and they can be administered by formulation into granules. An adjuvant refers to any compound, substance or composition that enhances the immune response against the protein when administered together (or successively) with the protein having immunological activity. A Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, *salmonella* toxin, Incomplete Freund's adjuvant (IFA), Complete Freund's adjuvant (CFA), ISCOMatrix, GM-CSF, CpG, O/W emulsion, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Examples of preferred salts include salts with an alkali metal, salts with a metal, salts with an organic base, salts with an organic acid and salts with an inorganic acid.

In some embodiments, the pharmaceutical agents or compositions of the present invention may further include a component that primes CTL. Lipids have been identified as agents or compositions capable of priming CTL in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1,000 mg, for example, 0.001 mg to 1,000 mg, for example, 0.1 mg to 10 mg, and can be administered once in a few days to few months. One skilled in the art can appropriately select a suitable dose.

(2) Pharmaceutical Agents or Compositions Containing Polynucleotides as Active Ingredient The pharmaceutical agents or compositions of the present invention can also contain nucleic acids encoding the peptide(s) disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors. See also, e.g., Wolff et al., Science 1990, 247: 1465-8; U.S. Pat. Nos. 5,580,859; 5,589,466; 5,804,566; 5,739,118; 5,736,524; 5,679,647; and WO 98/04720). Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can either be direct, wherein the patient is directly exposed to a polynucleotide-carrying vector, or indirect, wherein cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology can also be used for the present invention. See for example Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. Methods using the Peptides, Exosomes, APCS and CTLS

The peptides and polynucleotides of the present invention can be used for preparing or inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical agents or compositions of the present invention can be used for inducing CTLs, and in addition thereto, those including the peptides and polynucleotides can be also be used for inducing APCs as discussed in greater detail below.

(1) Method of Inducing Antigen-Presenting Cells (APCs)

The present invention provides methods of inducing APCs with high CTL inducibility using the peptides or polynucleotides of the present invention.

The methods of the present invention include the step of contacting APCs with the peptides of the present invention in vitro, ex vivo or in vivo. For example, the method contacting APCs with the peptides ex vivo or in vitro can include steps of:
  a: collecting APCs from a subject:, and
  b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any peptides of the present invention can be used by themselves or with other peptides of the present invention.

On the other hands, when the peptides of the present invention are administered to a subject, the APCs are contacted with the peptides in vivo, consequently, the APCs with high CTL inducibility are induced in the body of the subject. Thus, the present invention includes administering the peptides of the present invention to a subject. Similarly, when the polynucleotides of the present invention are administered to a subject in an expressible form, the peptides of the present invention are expressed and contacted with APCs in vivo, consequently, the APCs with high CTL inducibility are induced in the body of the subject. Thus, the present invention may also include administering the polynucleotides of the present invention to a subject. "Expressible form" is described above in section "IX. Pharmaceutical agents or compositions, (2) Pharmaceutical agents or compositions containing polynucleotides as the active ingredient".

The present invention may also include the step of introducing the polynucleotide of the present invention into an APCs so as to induce APCs with CTL inducibility. An illustrative example of such a method can include steps of:
  a: collecting APCs from a subject:, and
  b: introducing a polynucleotide encoding the peptide of the present invention.

Step b can be performed as described above in section "VI. Antigen-presenting cells".

Alternatively, the present invention provides a method for preparing an antigen-presenting cell (APC) which specifically induces CTL activity against CDC45L, wherein the method can include one of the following steps:
  (a) contacting an APC with a peptide of the present invention in vitro, ex vivo or in vivo; and
  (b) introducing a polynucleotide encoding a peptide of the present invention into an APC.

(2) Method of Inducing CTLs

Furthermore, the present invention provides methods for inducing CTLs using the peptides, polynucleotides, exosomes or APCs of the present invention.

The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs may include at least one step selected from the group consisting of:
a) contacting a CD8 positive T cell with an antigen-presenting cell and/or an exosome that presents on its surface a complex of an HLA antigen and a peptide of the preset invention; and
b) introducing a polynucleotide encoding a polypeptide that is capable of forming a TCR subunit recognizing a complex of a peptide of the present invention and an HLA antigen into a CD8 positive cell.

When the peptides, the polynucleotides, APCs, or exosomes of the present invention are administered to a subject, CTLs are induced in the body of the subject, and the strength of the immune response targeting the cancer cells is enhanced. Thus, the methods of the present invention includes the step of administering the peptides, the polynucleotides, the APCs or exosomes of the present invention to a subject.

Alternatively, CTLs can be also induced by using them ex vivo or in vitro, and after inducing CTL, the activated CTLs can be returned to the subject. For example, the method can include steps of:
  a: collecting APCs from a subject;
  b: contacting with the APCs of step a, with the peptide; and
  c: co-culturing the APCs of step b with CD8 positive cells.

The APCs to be co-cultured with the CD8 positive cells in above step c can also be prepared by transferring a gene that includes a polynucleotide of the present invention into APCs as described above in section "VI. Antigen-presenting cells", though the present invention is not limited thereto, and may therefore encompass any APCs that effectively present on its surface a complex of an HLA antigen and a peptide of the present invention.

Instead of such APCs, the exosomes that presents on its surface a complex of an HLA antigen and the peptide of the present invention can be also used. Namely, the present invention can include the step of co-culturing exosomes presenting on its surface a complex of an HLA antigen and the peptide of the present invention. Such exosomes can be prepared by the methods described above in section "V. Exosomes".

Furthermore, CTL can be induced by introducing a gene that includes a polynucleotide encoding the TCR subunit binding to the peptide of the present invention into CD8 positive cells. Such transduction can be performed as described above in section "VIII. T cell receptor (TCR)".

In addition, the present invention provides a method or process for manufacturing a pharmaceutical substance or composition inducing CTLs, wherein the method includes the step of admixing or formulating the peptide of the present invention with a pharmaceutically acceptable carrier.

(3) Method of Inducing Immune Response

Moreover, the present invention provides methods of inducing immune response against diseases related to CDC45L. Suitable diseases include cancer, examples of which include, but are not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer.

The methods of the present invention may include the step of administering agent (s) or composition(s) containing any of the peptides of the present invention or polynucleotides encoding them. The inventive methods also contemplate the administration of exosomes or APCs presenting any of the peptides of the present invention. For details, see the item of "IX. Pharmaceutical agents or compositions", particularly the part describing the use of the pharmaceutical agents or compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical agent or composition inducing immune response, wherein the method may include the step of admixing or formulating the peptide of the present invention with a pharmaceutically acceptable carrier.

Alternatively, the method of the present invention may include the step of administrating a vaccine or a pharmaceutical agent or composition, which contains:

(a) a peptide of the present invention;
(b) a nucleic acid encoding such a peptide as disclosed herein in an expressible form;
(c) an APC or an exosome presenting a peptide of the present invention on its surface; or
(d) a cytotoxic T cell of the present invention.

In the context of the present invention, cancer overexpressing CDC45L can be treated with these active ingredients. Examples of such cancers include, but are not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer. Accordingly, prior to the administration of the vaccines or pharmaceutical agents or compositions including the active ingredients, it is preferable to confirm whether the expression level of CDC45L in the cells or tissues to be treated is enhanced compared with normal cells of the same organ. Thus, in one embodiment, the present invention provides a method for treating cancer (over)expressing CDC45L, which method may include the steps of:
i) determining the expression level of CDC45L in cells or tissue(s) obtained from a subject with the cancer to be treated;
ii) comparing the expression level of CDC45L with normal control level; and
iii) administrating at least one component selected from the group consisting of (a) to (d) described above to a subject with cancer overexpressing CDC45L compared with normal control.

Alternatively, the present invention may provide a vaccine or pharmaceutical agent or composition that includes at least one component selected from the group consisting of (a) to (d) described above, for use in administrating to a subject having cancer overexpressing CDC45L. In other words, the present invention further provides a method for identifying a subject to be treated with a CDC45L polypeptide of the present invention, such method including the step of determining an expression level of CDC45L in subject-derived cells or tissue(s), wherein an increase of the level compared to a normal control level of the gene indicates that the subject may have cancer which may be treated with the CDC45L polypeptide of the present invention. Methods of treating cancer of the present invention are described in more detail below.

Any subject-derived cell or tissue can be used for the determination of CDC45L expression so long as it includes the objective transcription or translation product of CDC45L. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

A subject to be treated by the present method is preferably a mammal. Exemplary mammals include, but are not limited to, e.g., human, non-human primate, mouse, rat, dog, cat, horse, and cow.

According to the present invention, the expression level of CDC45L in cells or tissues obtained from a subject may be determined. The expression level can be determined at the transcription (nucleic acid) product level, using methods known in the art. For example, the mRNA of CDC45L may be quantified using probes by hybridization methods (e.g., Northern hybridization). The detection may be carried out on a chip, an array or as such. The use of an array may be preferable for detecting the expression level of CDC45L. Those skilled in the art can prepare such probes utilizing the sequence information of CDC45L. For example, the cDNA of CDC45L may be used as the probes. If necessary, the probes may be labeled with a suitable label, such as dyes, fluorescent substances and isotopes, and the expression level of the gene may be detected as the intensity of the hybridized labels.

Furthermore, the transcription product of CDC45L (e.g., SEQ ID NO: 17) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of CDC45L. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing substances, such as formamide.

Alternatively, the translation product may be detected for the diagnosis of the present invention. For example, the quantity of CDC45L protein (SEQ ID NO: 18) or the immunologically fragment thereof may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the CDC45L protein. Such antibodies against the peptides of the present invention and the fragments thereof are also provided by the present invention. Methods to prepare these kinds of antibodies for the detection of proteins are well known in the art, and any method may be employed in the present invention to prepare such antibodies and equivalents thereof.

As another method to detect the expression level of CDC45L gene based on its translation product, the intensity of staining may be measured via immunohistochemical analysis using an antibody against the CDC45L protein. Namely, in this measurement, strong staining indicates increased presence/level of the protein and, at the same time, high expression level of CDC45L gene.

The expression level of a target gene, e.g., the CDC45L gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells, by using a sample(s) previously collected and stored from a subject(s) whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of CDC45L gene in samples from subjects whose disease states are known. Furthermore, the control level can be derived from a database of expression patterns from previously tested cells. Moreover, according to an aspect of the present invention, the expression level of CDC45L gene in a biological sample may be compared to multiple control levels determined from multiple reference samples. It is preferred to use a control level determined from a reference sample derived from a tissue type similar to that of the subject-derived biological sample. Moreover, it is preferred to use the standard value of the expression levels of CDC45L gene in a population with a known disease state. The standard value may be obtained by any method known in the art. For example, a range of mean+/−2 S.D. or mean+/−3 S.D. may be used as the standard value.

When the expression level of CDC45L gene is increased as compared to the normal control level, or is similar/equivalent to the cancerous control level, the subject may be diagnosed with cancer to be treated.

The present invention also provides a method of (i) diagnosing whether a subject suspected to have cancer to be treated, and/or (ii) selecting a subject for cancer treatment, which method may include the steps of:

a) determining the expression level of CDC45L in cells or tissue(s) obtained from a subject who is suspected to have the cancer to be treated;

b) comparing the expression level of CDC45L with a normal control level;

c) diagnosing the subject as having the cancer to be treated, if the expression level of CDC45L is increased as compared to the normal control level; and d) selecting the subject for cancer treatment, if the subject is diagnosed as having the cancer to be treated, in step c).

Alternatively, such a method may include the steps of:

a) determining the expression level of CDC45L in cells or tissue(s) obtained from a subject who is suspected to have the cancer to be treated;

b) comparing the expression level of CDC45L with a cancerous control level;

c) diagnosing the subject as having the cancer to be treated, if the expression level of CDC45L is similar or equivalent to the cancerous control level; and d) selecting the subject for cancer treatment, if the subject is diagnosed as having the cancer to be treated, in step c).

The present invention also provides a diagnostic kit for diagnosing or determining a subject who is or is suspected to be suffering from cancer that can be treated with the CDC45L polypeptide of the present invention, which may also find use in assessing the prognosis of cancer and/or monitoring the efficacy or applicability of a particular cancer therapy, more particularly a cancer immunotherapy. Illustrative examples of suitable cancers includes, but are not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer. More particularly, the kit preferably may include at least one reagent for detecting the expression of the CDC45L gene in a subject-derived cell, such reagent being selected from the group of:

(a) a reagent for detecting mRNA of the CDC45L gene;

(b) a reagent for detecting the CDC45L protein or the immunologically fragment thereof; and (c) a reagent for detecting the biological activity of the CDC45L protein.

Examples of reagents suitable for detecting mRNA of the CDC45L gene may include nucleic acids that specifically bind to or identify the CDC45L mRNA, such as oligonucleotides that have a complementary sequence to a portion of the CDC45L mRNA. These kinds of oligonucleotides are exemplified by primers and probes that are specific to the CDC45L mRNA. These kinds of oligonucleotides may be prepared based on methods well known in the art. If needed, the reagent for detecting the CDC45L mRNA may be immobilized on a solid matrix. Moreover, more than one reagent for detecting the CDC45L mRNA may be included in the kit.

On the other hand, examples of reagents suitable for detecting the CDC45L protein or the immunologically fragment thereof may include antibodies to the CDC45L protein or the immunologically fragment thereof. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the CDC45L protein or the immunologically fragment thereof. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the CDC45L protein may be included in the kit.

The kit may contain more than one of the aforementioned reagents. The kit can further include a solid matrix and reagent for binding a probe against a CDC45L gene or antibody against a CDC45L peptide, a medium and container for culturing cells, positive and negative control reagents, and a secondary antibody for detecting an antibody against a CDC45L peptide. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers may include bottles, vials, and test tubes. The containers may be formed from a variety of materials, such as glass or plastic.

As an embodiment of the present invention, when the reagent is a probe against the CDC45L mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of CDC45L mRNA present in the sample. The detection sites may be configured in any suitably detectable shape and are typically in the shape of a bar or dot spanning the width of a test strip.

The kit of the present invention may further include a positive control sample or CDC45L standard sample. The positive control sample of the present invention may be prepared by collecting CDC45L positive samples and then assaying their CDC45L levels. Alternatively, a purified CDC45L protein or polynucleotide may be added to cells that do not express CDC45L to form the positive sample or the CDC45L standard sample. In the present invention, purified CDC45L may be a recombinant protein. The CDC45L level of the positive control sample is, for example, more than the cut off value.

In one embodiment, the present invention further provides a diagnostic kit including, a protein or a partial protein thereof capable of specifically recognizing the antibody of the present invention or an immunogenic fragment thereof.

Examples of the partial peptides and immunogenic fragments of proteins of the present invention contemplated herein include polypeptides composed of at least 8, preferably 15, and more preferably 20 contiguous amino acids in the amino acid sequence of the protein of the present invention. Cancer can be diagnosed by detecting an antibody in a sample (e.g., blood, tissue) using a protein or a peptide (polypeptide) of the present invention. Methods for preparing a peptide or protein of the present invention are as described above.

The method for diagnosing cancer of the present invention can be performed by determining the difference between the amount of anti-CDC45L antibody and that in the corresponding control sample as describe above. The subject is suspected to be suffering from cancer, if cells or tissues of the subject contain antibodies against the expression products (CDC45L) of the gene and the quantity of the anti-CDC45L antibody is determined to be more than the cut off value in level compared to that in normal control.

In another embodiment, a diagnostic kit of the present invention may include the peptide of the present invention and an HLA molecule binding thereto. A suitable method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. The complex may be used to quantify the antigen-peptide specific CTLs in the peripheral blood lymphocytes derived from the subject suspected to be suffering from cancer.

The present invention further provides methods and diagnostic agents for evaluating the immunological response of subject using peptide epitopes as described herein. In one embodiment of the invention, HLA restricted peptides as described herein may be used as reagents for evaluating or predicting an immune response of a subject. The immune response to be evaluated may be induced by contacting an immunogen with immunocompetent cells in vitro or in vivo. In certain embodiments, the substances or compositions employed as the reagent may be any substance or composition that may result in the production of antigen specific CTLs that recognize and bind to the peptide epitope(s). The peptide reagents need not be used as the immunogen. Assay systems that are used for such an analysis include relatively recent technical developments such as tetramers, staining for intracellular lymphokines and interferon release assays, or ELISPOT assays. In a preferred embodiment, immunocompetent cells to be contacted with peptide reagent may be antigen presenting cells including dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174:94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer consisting of the trimolecular complex and streptavidin. By means of fluorescently labeled streptavidin, the tetramer can be used to stain antigen specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et al, J. Clin. Invest. 100: 503-513, 1997 and Penna et al., J. Exp. Med. 174: 1565-1570, 1991) including peptides of the present invention. For example, patient PBMC samples from individuals with cancer to be treated can be analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele specific molecules present in the patient are selected for the analysis. The immunogenicity of the vaccine may be indicated by the presence of epitope-specific CTLs in the PBMC sample. The peptides of the invention may also be used to make antibodies, using techniques well known in the art (see, e.g., CURRENT PROTOCOLS IN IMMUNOLOGY, Wiley/Greene, NY; and Antibodies A Laboratory Manual, Harlow and Lane, Cold Spring Harbor Laboratory Press, 1989), which may find use as reagents to diagnose, detect or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein. For instance, the present invention provides a method for diagnosing or detecting a disorder characterized by expression of a CDC45L immunogenic polypeptide. Such methods involve determining expression of a CDC45L HLA binding peptide, or a complex of a CDC45L HLA binding peptide and an HLA class I molecule in a biological sample. The expression of a peptide or complex of peptide and HLA class I molecule can be determined or detected by assaying with a binding partner for the peptide or complex. In an preferred embodiment, a binding partner for the peptide or complex may be an antibody recognizes and specifically bind to the peptide. The expression of CDC45L in a biological sample, such as a tumor biopsy, can also be tested by standard PCR amplification protocols using CDC45L primers. An example of tumor expression is presented herein and further disclosure of exemplary conditions and primers for CDC45L amplification can be found in WO2003/27322.

Preferred diagnostic methods involve contacting a biological sample isolated from a subject with an agent specific for the CDC45L HLA binding peptide to detect the presence of the CDC45L HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and CDC45L HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The diagnostic methods of the present invention can be performed in either or both of in vivo and in vitro. Accordingly, biological sample can be located in vivo or in vitro in the present invention. For example, the biological sample can be a tissue in vivo and the agent specific for the CDC45L immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor cells collected from a subject to be diagnosed or treated.

Alternatively, the diagnosis can be performed using a method that allows direct quantification of antigen-specific T cells by staining with Fluorescein-labeled HLA multimeric complexes (e.g., Altman, J. D. et al., 1996, Science 274:94; Altman, J. D. et al., 1993, Proc. Natl. Acad. Sci. USA 90:10330). Staining for intracellular lymphokines, and interferon-gamma release assays or ELISPOT assays also has been provided. Multimer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

XI. Antibodies

The present invention further provides antibodies that bind to peptides of the present invention. Preferred antibodies specifically bind to peptides of the present invention and will not bind (or will bind weakly) to non-peptide of the present invention. Alternatively, antibodies bind to peptides of the invention as well as the homologs thereof. Antibodies against peptides of the invention can find use in cancer diagnostic and prognostic assays, and imaging methodologies. Similarly, such antibodies can find use in the treatment, diagnosis, and/or prognosis of other cancers, to the extent CDC45L is also expressed or overexpressed in cancer patient. Moreover, intracellularly expressed antibodies (e.g., single chain antibodies) may therapeutically find use in treating cancers in which the expression of CDC45L is involved, examples of which include, but are not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer.

The present invention also provides various immunological assays for the detection and/or quantification of the CDC45L protein (SEQ ID NO: 18) or fragments thereof including polypeptide consisting of amino acid sequences selected from the group consisting of SEQ ID NOs: 2, 3, 4, 7 and 12. Such assays may include one or more anti-CDC45L antibodies capable of recognizing and binding a CDC45L protein or fragments thereof, as appropriate. In the context of the present invention, anti-CDC45L antibodies binding to CDC45L polypeptide preferably recognize polypeptide consisting of amino acid sequences selected from the group consisting of SEQ ID NOs: 2, 3, 4, 7 and 12. A binding specificity of antibody can be confirmed with inhibition test. That is, when the binding between an antibody to be analyzed and full-length of CDC45L polypeptide is inhibited under presence of any fragment polypeptides consisting of amino acid sequence of SEQ ID NOs: 2, 3, 4, 7 and 12, it is shown that this antibody specifically binds to the fragment. In the context of the present invention, such immunological assays are performed within various immunological assay formats well known in the art, including but not limited to, various types of radioimmunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, the present invention contemplates immunological imaging methods capable of detecting cancers expressing CDC45L, examples of which include, but are not limited to, radioscintigraphic imaging methods using labeled antibodies of the present invention. Such assays find clinical use in the detection, monitoring, and prognosis of CDC45L expressing cancers, examples of which include, but are not limited to, such as testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer.

The present invention also provides antibodies that bind to the peptides of the invention. An antibody of the invention can be used in any form, for example as a monoclonal or polyclonal antibody, and may further include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but is preferably derived from a mammal such as a human, mouse, or rat, more preferably from a human. A human-derived peptide may be obtained from the nucleotide or amino acid sequences disclosed herein.

According to the present invention, the peptide to be used as an immunization antigen may be a complete protein or a partial peptide of the protein. A partial peptide may include, for example, the amino (N)-terminal or carboxy (C)-terminal fragment of a peptide of the present invention.

Herein, an antibody is defined as a protein that reacts with either the full length or a fragment of a CDC45L peptide. In a preferred embodiment, an antibody of the present invention can recognize fragment peptides of CDC45L consisting of amino acid sequence selected from the group consisting of SEQ ID NOs: 2, 3, 4, 7 and 12. Methods for synthesizing oligopeptide are well known in the arts. After the synthesis, peptides may be optionally purified prior to use as immunogen. In the context of the present invention, the oligopeptide (e.g., 9- or 10mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primates may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for the immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies may include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239: 1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584; 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Exemplary chromatography, with the exception of affinity includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of a peptide of the invention, by exposing an antibody of the invention to a sample presumed to contain a peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. Vectors and Host Cells

The present invention also provides a vector and host cell into which a nucleotide encoding the peptide of the present invention is introduced. A vector of the present invention may be used to keep a nucleotide, especially a DNA, of the present invention in host cell, to express a peptide of the present invention, or to administer a nucleotide of the present invention for gene therapy.

When E. coli is a host cell and the vector is amplified and produced in a large amount in E. coli (e.g., JM109, DH5 alpha, HB101 or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in E. coli should have the above characteristics to be amplified in E. coli. When E. coli, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the E. coli is the pelB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from Bacillus subtilis (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Although methods and materials similar or equivalent to those described herein can be used in the practice or testing of the present invention, suitable methods and materials are described. All publications, patent applications, patents, and other references mentioned herein are incorporated by reference in their entirety. In case of conflict, the present specification, including definitions, will control. In addition, the materials, methods, and examples are illustrative only and not intended to be limiting.

The following examples are presented to illustrate the present invention and to assist one of ordinary skill in making and using the same. The examples are not intended in any way to otherwise limit the scope of the invention.

EXAMPLES

Materials and Methods cDNA Microarray Analysis.

Gene expression profiles were generated by cDNA microarray analysis, as described previously (Nakamura T et al., Oncogene 2004; 23:2385-400, Taniwaki M et al., Int J Oncol 2006; 29:567-75). The raw data of microarray analysis is available upon request to Professor Y. Nakamura (Univ. Tokyo, Inst. Med. Sci.). The tissue samples from lung cancers and adjacent noncancerous normal lung tissues were obtained from surgical specimens, and all patients provided their written informed consent to participate in this study.

Mice.

Six-week-old female nonobese diabetic (NOD)/severe combined immunodeficiency (SCID) mice were purchased from Charles River Laboratories Japan. The mice were maintained at the Center for Animal Resources and Development of Kumamoto University, and they were handled in accordance with the animal care guidelines of Kumamoto University.

Cell Lines and HLA Expression.

The CDC45L and HLA-A*2402 positive human lung cancer cell lines EBC-1 and Lu99 were kindly provided by the Health Science Research Resources Bank (Tsukuba, Japan). C1R-A2402 cells, an HLA-A*2402 transfectant of human B lymphoblastoid cell line C1R expressing a trace amount of intrinsic HLA class I molecule (Karaki S, Kariyone A, Kato N, Kano K, Iwakura Y, Takiguchi M. HLA-B51 transgenic mice as recipients for production of polymorphic HLA-A, B-specific antibodies. Immunogenetics 1993; 37:139-42)[26], were a generous gift from Dr. Masafumi Takiguchi (Kumamoto University, Kumamoto, Japan). The CDC45L positive human pancreatic cancer cell line PANC1 (HLA-A*0201+, HLA-A*2402−) and the TAP-deficient and HLA-A*0201 positive cell line T2 were purchased from Riken Cell Bank. The expression of HLA-A2 and HLA-A24 were examined by flow cytometry with an anti-HLA-A2 monoclonal antibody (mAb), BB7.2 (One Lambda, Inc., Canoga Park, Calif.), and anti-HLA-A24 mAb (One Lambda, Inc.), respectively, in order to select the HLA-A24 and HLA-A2 positive blood donors for the assays. These cells were maintained in vitro in RPMI 1640 medium supplemented with 10% FCS in a 5% $CO_2$ atmosphere at 37 degrees C.

Patients, Blood Samples, and Tumor Tissues.

The research protocol for collecting and using PBMCs from donors was approved by the Institutional Review Board of Kumamoto University. The blood samples or cancerous tissues and adjacent non-cancerous tissues were obtained from patients at Kumamoto University Hospital during routine diagnostic procedures after obtaining written Informed consent. Blood samples were also obtained from healthy donors after receiving their written informed consent. All samples were randomly coded to mask their identities, and blood samples were stored at −80 degrees C. until use.

Reverse Transcription-PCR and Northern Blot Analysis.

The reverse transcription-PCR (RT-PCR) analysis of cell lines and normal or cancerous tissues was performed as described previously (Nakatsura T et al., Biochem Biophys Res Commun 2001; 281:936-44). The CDC45L primer sequences were 5'-CTGGTGTTGCACAGGCTGTCATGG-3' (SEQ ID NO: 19) (sense) and 5'-CGCACACGGTTAGAAGAGGAG-3' (SEQ ID NO: 20) (antisense). After normalization by beta-actin mRNA as a control, we compared the expression of CDC45L mRNA in the tissues and cell lines. A Northern blot analysis was performed as described previously using a CDC45L gene-specific cDNA probe (corresponding to 1245 to 1867 bp) (Nakatsura T et al., Biochem Biophys Res Commun 2003; 306:16-25).

Immunohistochemical Staining.

Immunohistochemical examination of human CDC45L was performed as described previously with some modification (Nakatsura T et al., Biochem Biophys Res Commun 2001; 281:936-44). Briefly, after deparaffination and rehydration of tissue sections, endogenous peroxide was quenched with 0.3% hydrogen peroxide in methanol for 15 min, and nonspecific binding was reduced by incubation with protein block serum-free reagent (Dako) for 10 min. After washing with buffer solution (0.1% Tween 20 and 0.5 M NaCl in 0.05 M Tris-HCl buffer), the primary antibody (anti-human CDC45L antibody produced in rabbit, 1:100 dilution, HPA000614, affinity purified, Sigma-Aldrich) diluted in Can Get Signal (R) immunostain Solution A (Toyobo Co., Osaka, Japan) was incubated with samples overnight at 4 degrees C. Thereafter, sections were rinsed carefully with buffer solution and incubated with a secondary antibody (Labeled Polymer-HRP, anti-mouse and anti-rabbit antibody, Dako) at room temperature. After three washes with buffer solution, the staining reaction was performed by incubation with 3,3'-diaminobenzidine solution (Liquid DAB+ Substrate Chromogen System, Dako). Slides were then lightly counterstained with hematoxylin, dehydrated in ethanol, and cleared in xylene. Sections of testis known to express CDC45L were used as positive controls for the anti-human CDC45L antibody. For negative controls, we replaced the primary antibody with normal rabbit IgG.

Peptides.

Human CDC45L derived peptides, carrying binding motifs for HLA-A*2402 encoded molecules, were selected using the BIMAS software program (Bioinformatics and Molecular Analysis Section, Center for Information Technology, NIH, Bethesda, Md.), and 16 peptides (10 nonamers and 6 decamers, purity >95%) were synthesized (AnyGen, Gwangju, Korea) (Table 1). Peptides were dissolved in dimethylsulfoxide at the concentration of 20 micro-g/mL and stored at −80 degrees C. Two HIV peptides, HLA-A24 restricted RYLRDQQLL (SEQ ID NO: 21) peptide (HIV-A24) and HLA-A2 restricted SLYNTYATL (SEQ ID NO: 22) peptide (HIV-A2), were used as negative controls (Komori H et al., Clin Cancer Res 2006; 12:2689-97).

TABLE 1

Candidate peptides derived from human CDC45L predicted to be bound to HLA-A24 (A*2402)

| Peptide | Position | Subsequence residue listing (SEQ ID NO:) | HLA-A24 binding score* |
| --- | --- | --- | --- |
| CDC45L-A24-9-237-1 | 237-245 | KYVTDVGVL (1) | 600 |
| CDC45L-A24-9-109-2 | 109-117 | VYNDTQIKL (2) | 396 |
| CDC45L-A24-9-294-3 | 294-302 | SYTAARFKL (3) | 220 |
| CDC45L-A24-9-556-4 | 556-564 | KFLDALISL (4) | 72 |
| CDC45L-A24-9-328-5 | 328-336 | KFQAMDISL (5) | 60 |
| CDC45L-A24-9-396-6 | 396-404 | HFIQALDSL (6) | 30 |
| CDC45L-A24-9-370-7 | 370-378 | KFLASDVVF (7) | 30 |
| CDC45L-A24-9-192-8 | 192-200 | EYHGTSSAM (8) | 25 |
| CDC45L-A24-9-541-9 | 541-549 | HFDLSVIEL (9) | 22 |
| CDC45L-A24-9-364-10 | 364-372 | HFGFKHKFL (10) | 20 |
| CDC45L-A24-10-109-11 | 109-118 | VYNDTQIKLL (11) | 360 |
| CDC45L-A24-10-556-12 | 556-565 | KFLDALISLL (12) | 86 |
| CDC45L-A24-10-271-13 | 271-280 | SFEYDLRLVL (13) | 36 |
| CDC45L-A24-10-313-14 | 313-322 | EFLADMGLPL (14) | 30 |
| CDC45L-A24-10-21-15 | 21-30 | LFVASDVDAL (15) | 30 |
| CDC45L-A24-10-459-16 | 459-468 | LFSRPASLSL (16) | 20 |

*Binding scores were calculated by using BIMAS software (http://bimas.dcrt.nih.gov/cgi-bin/molbio/ken_parker_comboform).

Generation of CDC45L Reactive Human CTLs and Assays of CTL Responses.

PBMCs were isolated from HLA-A24 or HLA-A2 positive Japanese healthy donors and lung cancer patients, and the peripheral monocyte-derived dendritic cells (DCs) were generated as described previously (Harao M et al., Int J Cancer 2008; 123:2616-25, Naito K et al., Int J Oncol 2006; 28:1481-9). The DCs were pulsed with 20 micro-g/mL of the candidate peptides in the presence of 4 micro-g/mL beta 2-microglobulin (Sigma-Aldrich) for 2 h at 37 degrees C. in AIM-V (Invitrogen) supplemented with 2% heat-inactivated autologous plasma. The cells were then irradiated (40 Gy) and incubated with the isolated $CD8^+$ T cells as described previously (Imai K et al., Clin Cancer Res 2008; 14:6487-95, Harao M et al., Int J Cancer 2008; 123:2616-25). Two additional stimulations with peptide-loaded autologous PHA-blasts were performed on days 7 and 14. The PHA-blasts were generated as described previously (Inoue M et al., Immunol Lett 2009; 126:67-72), and these PHA-blasts ($5 \times 10^5$) were pulsed with 20 micro-g/mL peptides for 3 h, irradiated (100 Gy) and cultured with the $2 \times 10^6$ $CD8^+$ T cells in the presence of 10 ng/mL human recombinant IL-7 (Wako, Osaka, Japan). After 2 days, the cultures were supplemented with 20 IU/mL human recombinant IL-2 (PeproTec, Inc.).

Six days after the last stimulation, the antigen-specific responses of the induced CTLs were investigated. Two additional weekly stimulations with peptide-loaded autologous PHA-blasts were carried out on day 7 and 14. Autologous CD $14^-$ $CD8^-$ cells enriched with $CD4^+$ T cells were cultured with PHA (2 micro-g/mL) and human recombinant IL-2 (100 IU/mL) for 2 days, and cells were washed with PBS and cultured with human recombinant IL-2 (100 IU/mL) for additional three days. These PHA-blasts ($5 \times 10^5$) were pulsed with 50 micro-g/mL peptides for 2 hours at 37 degrees C. in AIM-V (Invitrogen) supplemented with 2% heat-inactivated autologous plasma. The cells were then irradiated (100 Gy) and incubated with the $2 \times 10^6$ $CD8^+$ T cells. These cultures were set up in 24-well plates using the medium supplemented with 5 ng/mL human recombinant IL-7, IL-2, and IL-15. Six days after the last stimulation, the antigen-specific responses of the induced CTLs were investigated by an IFN-gamma ELISPOT assay, CD107a mobilization assay and $^{51}Cr$ release assay as described previously (Komori H et al. Clin Cancer Res 2006; 12: 2689-97) and below.

CD107a Mobilization Assay.

To identify degranulating $CD8^+$ T lymphocytes stimulated with epitope peptides, the CD107a exposed on the cell surface was analyzed by flow cytometry (Rubio V et al., Nat Med 2003; 9:1377-82, Betts M R et al., J Immunol Methods 2003; 281:65-78). A CD107a mobilization assay was performed with an immunocyte CD107a detection kit (MBL, Nagoya, Japan) according to the manufacturer's instructions. The induced CTLs were suspended in a final concentration of $2 \times 10^6$ cells/mL of AIM-V supplemented with 2% heat-inactivated autologous plasma, and 150 micro-L of the cell suspension was added to each well of a 96-well, round-bottomed microplate. The CDC45L derived peptide or control HIV peptide (1 micro-g/ml) was added as a stimulant, and FITC-labeled anti-human CD107a mAb or FITC-labeled isotype control mouse IgG1 and monensin were added to each well. Cells were cultured for 5 h at 37 degrees C. After culture, the cells were stained with PE-conjugated anti-human CD8a (Biolegend) and analyzed by flow cytometry (FACScan; BD Biosciences).

Generation of CDC45L Knockdown Cells.

To knock down the expression of CDC45L in lung cancer cells, CDC45L small interfering (si) RNAs (human Cdc45 siRNA, sc-35044: a pool of three target-specific 20-25 nt siRNAs; Santa Cruz) were added at a final concentration of 150 nM to 40-60% confluent cells. Lipofectamine™ 2000 (Invitrogen) was used to transfect the siRNAs into cells, according to the manufacturer's instructions. GFP siRNAs were used as an irrelevant control. The treated cells were washed once with PBS, and adherent cells were collected at 72 h after transfection and used as target cells for the $^{51}Cr$-release assay. To investigate the ability of siRNA to suppress CDC45L expression, western blot analysis was performed as described previously (Nakatsura T et al., Biochem Biophys Res Commun 2003; 306:16-25). Cancer cells were washed once with PBS at 48 h after transfection, and adherent cells were collected and lysed to analyze the expression levels of CDC45L for comparison with those of negative control cells. Beta-actin was used as the internal control. Rabbit polyclonal antibody reactive to CDC45L (sc-20685, Santa Cruz Biotechnology) was used as the primary antibody.

Human CTL Responses Against Cancer Cell Lines.

The frequency of cells producing interferon (IFN)-gamma per $1 \times 10^5$ CTLs upon stimulation with Lu99 cells ($1 \times 10^4$/well) or peptide-pulsed C1R-A2402 and T2 cells ($1 \times 10^4$/well) was analyzed by an ELISPOT assay (Human IFN-gamma ELISPOT kit, BD Biosciences) as previously described (Komori H et al., Clin Cancer Res 2006; 12:2689-97, Bourgault V I et al., Cancer Res 2004; 64:8761-6). The CTLs were co-cultured with cancer cells or peptide-pulsed C1R-A2402 and T2 cells as target cells ($5 \times 10^3$/well) at the indicated effector-to-target ratio, and a standard $^{51}Cr$-release assay was performed as described previously (Yokomine K et al., Int J Cancer 2009; 126:2153-63, Monji M et al., Clin Cancer Res 2004; 10:6047-57). The blocking of HLA-class I by anti-human HLA class I mAb, W6/32 (IgG2a, Santa Cruz Biotechnology), or HLA-class II by anti-human HLA-DR mAb (IgG2a, BD Biosciences), was performed as described previously (Komori H et al., Clin Cancer Res 2006; 12:2689-97, Makita M et al., Clin Cancer Res 2002; 8:2626-31).

Adoptive Immunotherapy Model.

Experimental adoptive immunotherapy was performed as described previously (Imai K et al., Clin Cancer Res 2008; 14:6487-95, Komori H et al., Clin Cancer Res 2006; 12:2689-97). Briefly, Lu99 cells ($3 \times 10^6$ cells/mouse) positive for both endogenous CDC45L and HLA-A24 were subcutaneously inoculated into the right flanks of NOD/SCID mice. When the tumor size reached approximately 25 $mm^2$ on day 7, the CDC45L specific CTL lines induced from two healthy donors by in vitro stimulation with a mixture of CDC45L-A24-9-109-2 (SEQ ID NO: 2), CDC45L-A24-9-294-3 (SEQ ID NO: 3) and CDC45L-A24-9-556-4 (SEQ ID NO: 4) peptides or CTL lines induced by stimulation with irrelevant HLA-A24 restricted HIV peptide were suspended in 100 micro-L of PBS and injected intravenously ($4 \times 10^6$ cells/mouse). The intravenous injection of CTLs was repeated on day 14. The tumor size was evaluated twice a week using calipers to measure two perpendicular diameters.

Statistical Analysis.

Two-tailed Student's t-test was used to evaluate the statistical significance of differences in ELISPOT data and tumor sizes between the treatment groups. P values less than 0.05 were considered to be statistically significant. The statistical analysis was performed with a commercial statistical software package (StatView 5.0, Abacus Concepts, Calabasas, Calif.).

Results

Identification of CDC45L Gene Overexpression in Lung Cancer Based on cDNA Microarray Analyses.

Genome-wide cDNA microarray containing 27,648 genes was used to examine the gene expression profiles of 18 lung cancer tissues and their adjacent normal counterparts. cDNA microarray analysis revealed markedly enhanced expression of the CDC45L gene in lung cancer tissues in all 12 of the small-cell lung cancer patients (average relative expression ratio: 163,087; range: 81,204-369,309) and 4 of the 6 non-small cell lung cancer patients (average relative expression ratio: 15,170; range: 0.08-40,131) (Table 2). Therefore, CDC45L was selected to be characterized as a novel TAA of lung cancer. The expression level of the CDC45L gene was also enhanced in the majority of several other malignancies, including prostate, breast and bladder cancers, based on the cDNA microarray analyses (Table 2).

TABLE 2

Overexpression of CDC45L gene in lung cancer and various malignancies investigated by cDNA microarray analyses.

| Cancerous tissue | n | Positive rate* (%) | Relative expression ratio (mean) |
| --- | --- | --- | --- |
| Small cell lung cancer | 12 | 100% | 163,087 |
| Prostate cancer | 3 | 100% | 36,985 |
| Breast cancer | 8 | 75% | 8,648 |
| Bladder cancer | 13 | 69% | 2,194 |
| Non small cell lung cancer | 6 | 67% | 15,170 |
| CML | 3 | 33% | 8,606 |
| Soft tissue tumor | 4 | 25% | 9,258 |
| Esophagus | 25 | 16% | 2,378 |
| Gastric cancer | 3 | 0% | 1 |

*The relative expression ratio (cancer/normal tissue) >5 was considered to be positive.

Expression of CDC45L mRNA in Normal Tissues, Cancer Cell Lines, and Lung Cancer Tissues.

The expression of the CDC45L gene in normal tissues at the mRNA level was analyzed using RT-PCR and a Northern blot analysis. A semiquantitative RT-PCR analysis of CDC45L in the normal tissues revealed that it was faintly expressed only in testis and breast (FIG. 1A). A Northern blot analysis in normal tissues using CDC45L cDNA as a probe revealed that it was not expressed in twenty-two vital organs except testis (FIG. 1B), in accordance with the results of the RT-PCR analysis. In contrast, the expression of the CDC45L gene was detected in all of nine lung cancer cell lines using an RT-PCR analysis (FIG. 1C). Subsequently, the expression of the CDC45L gene was analyzed by using an RT-PCR analysis in the lung cancer tissues. In 7 of 8 NSCLC patients, CDC45L mRNA was strongly expressed in cancer tissues (FIG. 1D upper). In addition, the expression of the CDC45L gene was analyzed using an RT-PCR analysis in the cancer tissues and their adjacent normal counterparts, which were surgically resected. The expression of the CDC45L gene was detected in all of 4 lung cancer tissues, but little expression was detected in their normal counterparts (FIG. 1D lower). Furthermore, RT-PCR analyses of various cancer cell lines derived from gastric, hepatobiliary, breast, prostate and colorectal cancers revealed that CDC45L gene is also expressed in many of these cancer cell lines (FIG. 1E).

To investigate the expression of CDC45L at the protein level, immunohistochemical analysis of lung cancer tissues and normal tissues was performed. 26 samples of lung cancer tissues, consisting of 12 adenocarcinomas (7 of the 12 were bronchioalveolar carcinomas), 8 squamous cell carcinomas, and 6 small cell carcinomas were studied. All 26 samples exhibited strong nuclear staining of CDC45L and weak cytoplasmic staining (FIG. 1F). No staining or very weak staining was observed in normal adjacent lung tissues (FIG. 1F). CDC45L was expressed in testis, but no staining or very week staining was observed in other types of normal adult human tissues, including brain, heart, liver, kidney, stomach, small intestine, colon, pancreas, skin, spleen, and thymus (FIG. 1F and data not shown). Collectively, the protein expression levels of CDC45L in human lung cancers were evidently much higher than those in normal adult tissues, with the exception of testis. These results are consistent with the results from RT-PCR and Northern blot analyses (FIGS. 1A, B and D).

Identification of CDC45L-Derived and HLA-A24 Restricted CTL Epitopes in Healthy donors.

To identify HLA-A24 restricted and CDC45L derived CTL epitopes, 16 candidate peptides that were predicted to have high binding affinity to HLA-A24 were selected according to HLA-peptide binding prediction software provided by the NIH BIMAS (Table 1). To test which peptide could induce peptide-reactive CTLs, the CD8$^+$T cells sorted from the PBMCs of healthy donors were incubated with the autologous monocyte-derived DCs pulsed with the mixture of four peptides selected from these 16 CDC45L peptides. After two additional weekly stimulations with peptide-loaded autologous PHA-blasts, the cytotoxic activity against the peptide-pulsed C1R-A*2402 cells was examined by an IFN-gamma ELISPOT assay (FIG. 2). CD8$^+$T cells sorted from the PBMCs of two HLA-A24 positive healthy donors were stimulated with autologous monocyte-derived DCs pulsed with a mixture of 4 of the 16 CDC45L peptides. The frequency of CD8$^+$T cells specific to the CDC45L derived peptides in the resulting CTL lines was examined by an IFN-gamma ELISPOT assay (FIG. 3). Background controls were stimulated with C1R-A2402 cells pulsed with irrelevant HIV-A24 peptide. The generated CTL lines reproducibly produced a large amount of IFN-gamma upon stimulation with C1R-A2402 cells pulsed with CDC45L-A24-9-109-2 , $^{109}$VYNDTQIKL$^{117}$ (SEQ ID NO: 2), CDC45L-A24-9-294-3, $^{294}$SYTAARFKL$^{302}$ (SEQ ID NO: 3), CDC45L-A24-9-556-4, $^{556}$KFLDALISL$^{564}$ (SEQ ID NO: 4), CDC45L-A24-9-370-7, $^{370}$KFLASDVVF$^{378}$ (SEQ ID NO: 7), or CDC45L-A24-10-556-12 , $^{556}$KFLDALISLL$^{565}$ (SEQ ID NO: 12) peptides. These results suggest that these five CDC45L derived peptides are immunogenic.

Figure 4:
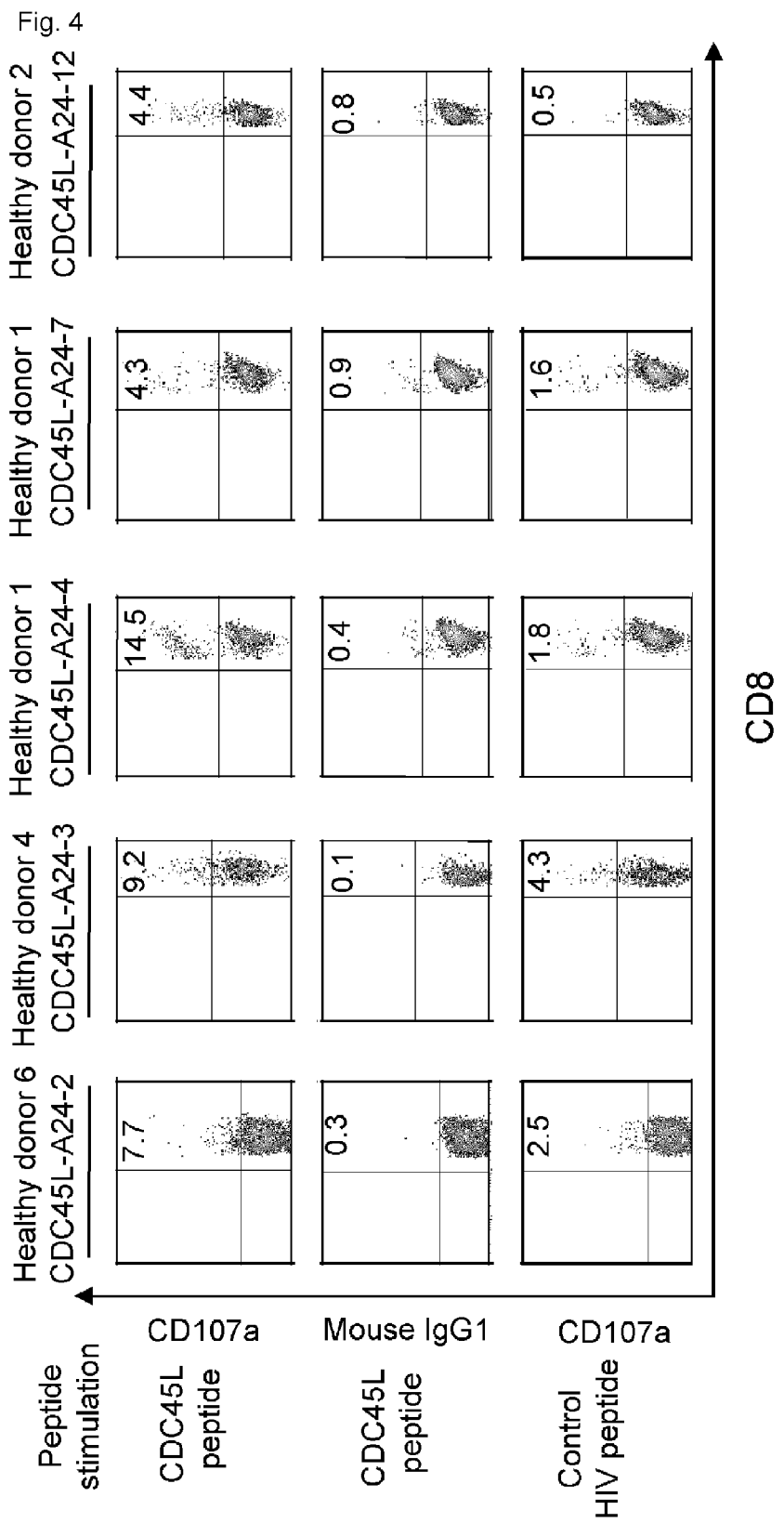
[FIG. 4]

To further analyze the CTL-stimulating capacity of these five immunogenic peptides, a CD107a mobilization assay was performed to evaluate the antigen-specific secretion of the cytolytic granule content by CTLs (Rubio V et al., Nat Med 2003; 9:1377-82, Betts M R et al. J Immunol Methods 2003; 281:65-78). A significantly higher proportion of CD8$^+$ T cells was stained by anti-CD107a mAb when the CTL lines generated by stimulation with one of these five immunogenic peptides were re-stimulated with their cognate peptides, as compared to re-stimulation with an irrelevant HIV-A24 peptide (FIG. 4).

Establishment of CTL Lines Specific to CDC45L-Derived Peptides in Lung Cancer Patients.

CDC45L specific CTLs were generated from the PBMCs of lung cancer patients positive for HLA-A24 by stimulation with the CDC45L-A24-9-109-2 (SEQ ID NO: 2), CDC45L-A24-9-294-3 (SEQ ID NO: 3), CDC45L-A24-9-556-4 (SEQ ID NO: 4), CDC45L-A24-9-370-7 (SEQ ID NO: 7) or CDC45L-A24-10-556-12 (SEQ ID NO: 12) peptide. These CTL lines produced a significantly large amount of IFN-gamma in response to CDC45L derived peptides in IFN-gamma ELISPOT assays (FIG. 5A). In addition, these CTL lines exhibited cytotoxic activity against C1R-A2402 cells pulsed with the five CDC45L derived peptides, but not against C1R-A2402 cells pulsed with irrelevant HIV-A24 peptide, in $^{51}$Cr-release assays (FIG. 5B). These results indicate that these CTLs had a peptide-specific cytotoxic activity.

Natural Processing of CDC45L CTL Epitopes in Cancer Cells.

The ability of these CTLs to kill human lung cancer cell lines that naturally expressed both CDC45L and HLA-A24 were examined. Lu99 and EBC-1 cells (CDC45L+, HLA-A24+), Lu99 and EBC-1 cells transfected with CDC45L specific siRNAs (CDC45L−, HLA-A24+), Lu99 and EBC-1 cells transfected with control GFP siRNAs (CDC45L+, HLA-A24+) (FIG. 5C) and A549 cells (CDC45L+, HLA-A24−) (FIG. 5C) were used as target cells. As shown in FIG. 5D, the CTL lines generated from the healthy donor-4 (bottom panel, left) and lung cancer patient-18 (bottom panel, right) by stimulation with CDC45L-A24-9-109-2 (SEQ ID NO: 2) and CDC45L-A24-9-556-4 (SEQ ID NO: 4) peptides, respectively, exhibited cytotoxicity against Lu99 cells and Lu99 cells transfected with control GFP siRNAs, but not against Lu99 cells transfected with CDC45L specific siRNAs (bottom panels) and A549 cells (bottom panel, left). Similarly, the CTLs generated from lung cancer patient-1 by stimulation with CDC45L-A24-9-294-3 (SEQ ID NO: 3) peptide exhibited cytotoxicity to EBC-1 and EBC-1 cells transfected with GFP siRNAs, but not to EBC-1 cells transfected with CDC45L specific siRNAs and A549 cells (upper panel, left). Also, the CTLs generated from lung cancer patients 3 and 8 stimulated with and CDC45L-A24-9-370-7 (SEQ ID NO: 7) peptide exhibited cytotoxicity to EBC-1 and EBC-1 cells transfected with GFP siRNAs, but not to EBC-1 cells transfected with CDC45L-specific siRNAs and A549 cells (upper panel, middle, right). Among the five immunogenic CDC45L derived peptides, three, CDC45L-A24-9-109-2 (SEQ ID NO: 2), CDC45L-A24-9-294-3 (SEQ ID NO: 3) and CDC45L-A24-9-556-4 (SEQ ID NO: 4), elicited CDC45L specific CTLs that could effectively lyse lung cancer cells that naturally expressed both CDC45L and HLA-A24. These results suggest that these three CDC45L derived peptides could be naturally processed and presented in the context of HLA-A24 molecules in cancer cells.

To confirm that the CTLs specific to the three CDC45L derived peptides recognize the target cells in an HLA-class I-restricted manner, mAb specific to HLA-class I (W6/32) was used to block the recognition by CTLs. IFN-gamma production and cytotoxicity were significantly inhibited by the blocking mAb against HLA-class I, but not by control anti-HLA-class II mAb (FIGS. 6A and B). These results clearly indicate that these induced CTLs recognize the target cells expressing endogenous CDC45L in an HLA-class I-restricted manner.

CDC45L-9-556-4 (SEQ ID NO: 4), $^{556}$KFLDALISL$^{564}$, peptide can induce CTLs restricted by both HLA-A2 (A*0201) and HLA-A24 (A*2402)

CDC45L-A2-9-556-4 (also referred herein as CDC45L-A24-9-556-4), $^{556}$KFLDALISL$^{564}$ (SEQ ID NO: 4), peptide was predicted to have a high binding affinity to not only HLA-A24 (A*2402) but also HLA-A2 (A*0201), according to HLA-peptide binding prediction software SYFPEITHI (Institute for Immunology, University of Tubingen, Tubingen, Germany, www.syfpeithi.de/). HLA-A*2402 is the most frequent HLA class I allele in the Japanese population, and HLA-A*0201 is one of the most common HLA allele in various ethnic groups, including Asian, African, Afro-American, and Caucasian (Browning M et al. Immunol Today 1996; 17:165-70). Thus, it was hypothesized that the CDC45L-A2-9-556-4 (SEQ ID NO: 4) peptide is a candidate common CTL epitope restricted by both HLA-A2 and HLA-A24. To determine whether the CDC45L-A2-9-556-4 (SEQ ID NO: 4) peptide can bind to HLA-A2 molecules, an HLA-A2 stabilizing assay was performed with T2 cells, as described previously (Yokomine K et al., Int J Cancer 2009; 126:2153-63). The CDC45L-A2-9-556-4 (SEQ ID NO: 4) peptide bound to HLA-A2 molecules with a superior capacity to stabilize HLA-A2 compared to the HIV-A2 peptide, which was used as the positive control (data not shown). Thus, it was confirmed the actual binding of the peptide to HLA-A2.

Next, CDC45L-A2-9-556-4 (SEQ ID NO: 4) specific CTLs from the PBMCs of a healthy donor positive for HLA-A2 (A*0201) was generated by stimulation with the CDC45L-A2-9-556-4 (SEQ ID NO: 4) peptide. The CTL lines generated from the HLA-A2 positive healthy donor produced IFN-gamma specifically in response to re-stimulation with T2 cells pulsed with the peptide (FIG. 7A). In addition, the generated CTL lines exhibited cytotoxicity against T2 cells pulsed with the CDC45L-A2-9-556-4 (SEQ ID NO: 4) peptide, but not against T2 cells loaded with the irrelevant HIV-A2 peptide or C1R-A2402 cells loaded with the CDC45L-A2-9-556-4 (SEQ ID NO: 4) peptide (FIG. 7B). These results indicate that these CTLs mediated peptide-specific cytotoxicity in an HLA-A2 restricted manner. Furthermore, the generated CTL lines could effectively lyse Panc1 cells that expressed endogenous CDC45L and HLA-A2 (A*0201) molecules but not HLA-A24, and the cytotoxicity was significantly inhibited by blocking mAb against HLA-class I (W6/32) but not by control anti-HLA-class II mAb, as determined by a $^{51}$Cr-release assay (FIG. 7C).

Figure 7:
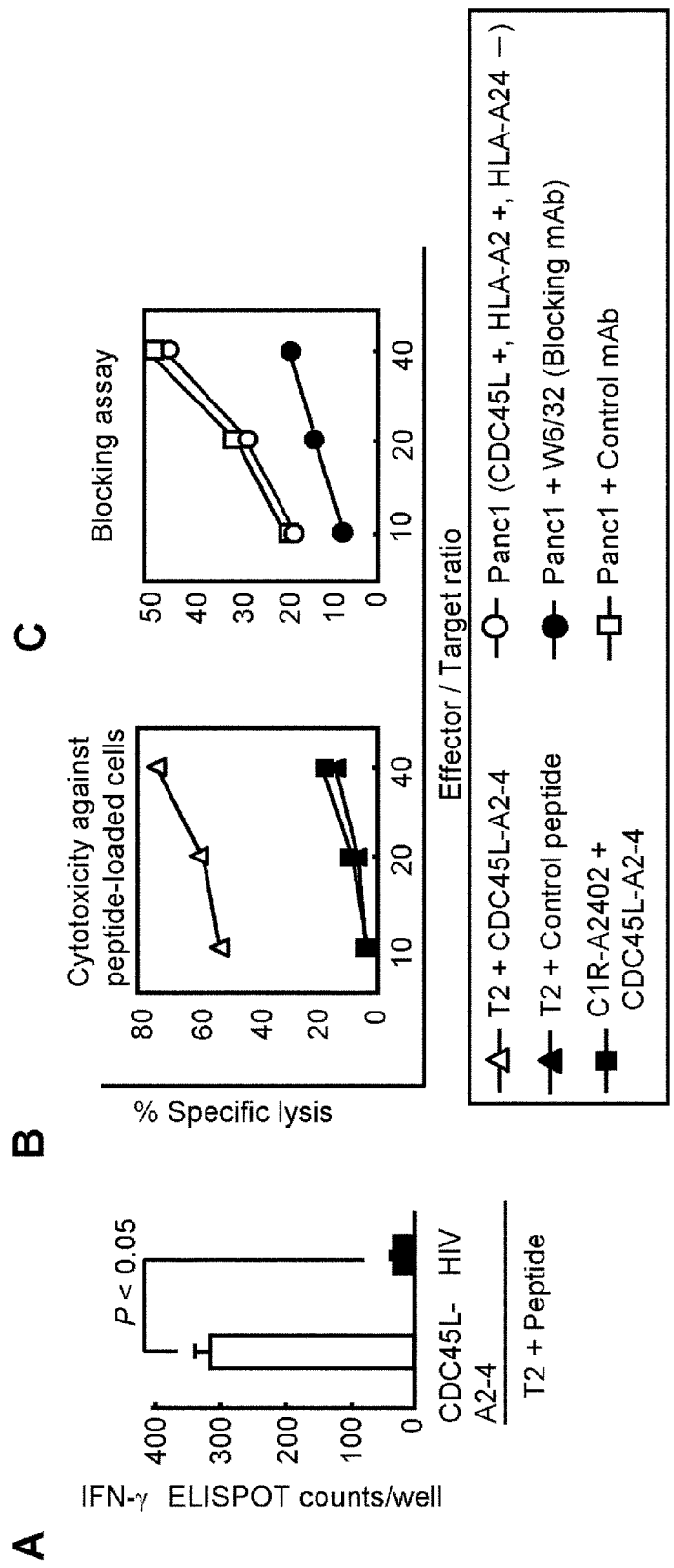
[FIG. 7]

These results clearly indicate that CDC45L-A2-9-556-4 (SEQ ID NO: 4) peptide was naturally processed from CDC45L protein and presented not only in the context of HLA-A24 but also in the context of HLA-A2 to be recognized by CDC45L-A2-9-556-4 (SEQ ID NO: 4) peptide-induced CTLs (FIGS. 5D, 6 and FIG. 7). Thus, CDC45L-A2-9-556-4 (SEQ ID NO: 4) is a common CTL epitope restricted by both HLA-A2 and HLA-A24, and this peptide will be applicable to immunotherapy for more than 80% of Japanese patients with cancer expressing CDC45L.

In Vivo Antitumor Activity of CDC45L Reactive Human CTLs in NOD/SCID Mice.

To assess the therapeutic efficacy of CDC45L reactive CTL inoculation into immunocompromised mice implanted with CDC45L positive human lung cancer cells, Lu99 cells was subcutaneously inoculated into NOD/SCID mice. After 7 days, when the tumor diameters reached approximately 5×5 mm, mice were intravenously injected with human CTLs generated by the stimulation of CD8$^+$ T cells with autologous monocyte-derived DCs (day 0) and autologous PHA-blasts (days 7 and 14) pulsed with a mixture of CDC45L-A24-9-109-2 (SEQ ID NO: 2), CDC45L-A24-9-294-3 (SEQ ID NO: 3) and CDC45L-A24-9-556-4 (SEQ ID NO: 4) peptides or an irrelevant HIV-A24 peptide. Before the inoculation of CTLs into mice, the peptide-specific cytotoxic activity of CTLs was assessed (FIG. 8). The CTL lines generated from two healthy donors that were HLA-A24 positive produced IFN-gamma specifically in response to re-stimulation with C1R-A2402 cells pulsed with the peptides, except for the CDC45L-A24-9-294-3 (SEQ ID NO: 3) peptide in healthy donor-5 (FIG. 8A). In addition, the mixture of CDC45L peptides elicited CTLs that could effectively lyse Lu99 cells, and the cytotoxicity was significantly inhibited by blocking mAb specific to HLA-class I in a $^{51}$Cr-release assay (FIG. 8B). On the other hand, the CTL lines exhibited specific lysis against CDC45L-A24-9-109-2 (SEQ ID NO: 2) peptide-pulsed C1R-A2402, but not against CDC45L-A24-9-294-3 (SEQ ID NO: 3), CDC45L-A24-9-556-4 (SEQ ID NO: 4) or irrelevant HIV-A24 peptide-pulsed C1R-A2402 in both healthy donor-4 and -5 (FIG. 8C).

The tumors in the mice inoculated with the CDC45L stimulated CTLs (n=5; mean+/−standard deviation [SD], 108+/−65 mm$^2$) were significantly smaller than those of mice inoculated with the control HIV peptide-induced CD8$^+$ T cells (n=5; mean+/−SD, 271+/−94 mm$^2$) or with PBS alone (n=5; mean+/−SD, 297+/−44 mm$^2$) on day 42 after the inoculation of Lu99 cells (two-tailed Student's t-test, *$P<0.05$, **$P<0.01$; FIG. 8D). The results clearly indicate the efficacy of adoptive transfer therapy of CDC45L specific human CTLs against CDC45L positive human tumors in NOD/SCID mice.

In conclusion, CDC45L antigen is suggested to be highly immunogenic and a promising target for peptide-based immunotherapy of lung cancer without causing autoimmune phenomena.

Discussion

In the current study, novel TAA, Cell division cycle 45-like (CDC45L), was identified using a cDNA microarray analysis of lung cancer. The microarray data showed that CDC45L was overexpressed in prostate, breast and bladder cancers as well as in lung cancer. In accordance with the data obtained from the cDNA microarray analysis of CDC45L gene expression in lung cancer tissues, the expression of the CDC45L gene was detected in all of 4 lung cancer tissues, but not in their normal counterparts. Furthermore, CDC45L expression was barely detectable in many vital organs except testis in the RT-PCR and Northern blot analyses in normal tissues. These results suggest that targeting CDC45L could be a novel immunotherapeutic approach for these cancers, without causing autoimmune diseases.

It was also found that CDC45L-derived immunogenic peptides, CDC45L-A24-9-109-2, CDC45L-A24-9-204-3 and CDC45L-A24-9-556-4, could induce epitope-specific CTLs in BALB/c mice immunized with peptides emulsified in incomplete Freund adjuvant (data not shown). BALB/c mice immunized with the CDC45L-derived and H2-Kd-restricted peptides, CDC45L-A24-9-109-2 and CDC45L-A24-9-204-3, did not exhibit pathological changes, such as lymphocyte infiltration or tissue destruction, and had no signs of autoimmune diseases, such as weight loss, diarrhea and skin abnormalities, during a long-term observation period (unpublished data). These results also indicate that CDC45L-derived peptides could induce peptide-reactive CTLs in vivo without causing autoimmune diseases in mice.

It is well known that CDC45L has a critical role in the initiation and elongation steps of DNA replication, therefore loss of CDC45L is difficult to occur in cancers cells. In a previous study, Pollok et al. showed that the CDC45L protein level was consistently higher in human cancer-derived cells compared with primary human cells, and CDC45L expression is tightly associated with proliferating cell populations (Pollk S, et al. FEBS J 2007; 274: 3669-3684.). Additional previous studies suggested that the upregulation of CDC45L was dependent on the dysplasia grade and lymph node status (Li J N, et al. BMC Cancer 2008, 395: 1-8.). Furthermore, Feng et al. recently reported that down-regulation of CDC45L gene expression by the specific si-RNA markedly inhibited the growth of cancer cell lines such as Hela and HepG2 cells suggesting that CDC45L was an useful target for anticancer therapy (Feng D, et al. Cancer Res 2003; 63: 7356-7364.). A recent report summarized that the objective response rate of cancer vaccine in clinical trials was low (2.6%) (Rosenberg S A, et al. Nat Med 2004; 10: 909-15.). One possible reason is that the immune escape of cancer cells attributed to deletion, mutation, or a down-regulation of the TAAs occurs as a consequence of therapeutically driven immune selection. Based on the standpoint that tumor cells cannot lose antigens which are required for tumorigenesis, CDC45L is considered as a possible candidate TAA useful for anticancer immunotherapy. In the present invention, five HLA-A24-restricted CDC45L epitope peptides, CDC45L-A24-9-109-2, CDC45L-A24-9-294-3, CDC45L-A24-9-556-4, CDC45L-A24-9-370-7 and CDC45L-A24-10-556-12, which could generate HLA-A24-restricted human CTLs from PBMCs by in vitro stimulation with the peptides, were identified. Furthermore, it was found that the CDC45L-reactive CTLs could be also generated from PBMCs isolated from lung cancer patients by stimulation with these five peptides. In four CDC45L epitope peptides, CDC45L-A24-9-109-2, CDC45L-A24-9-294-3, CDC45L-A24-9-556-4 and CDC45L-A24-9-370-7, the peptide-induced CTLs could kill not only the C1R-A*2402 cells pulsed with the cognate peptide, but also the cancer cell lines expressing CDC45L in an HLA-A24-restricted manner. These data suggest that these CDC45L peptides are naturally processed from CDC45L protein in cancer cells and presented onto the cell surface in the context of HLA-A24 molecules to be recognized by the CTLs. HLA-A24 (A*2402) is known to be one of the most common HLA-alleles in the Japanese population, with an estimated antigen frequency of 60%, and is also present in Caucasians, with an estimated antigen frequency of 10%. The identification of the HLA-A24-restricted and CDC45L-derived CTL epitopes has also been suggested to be useful for the immunotherapy of many patients with lung cancer, all over the world especially in Asians (Date, Y., et al. Tissue Antigens, 1996; 47: 93-101.).

In conclusion, the results disclosed herein suggest that CDC45L is a novel TAA of which epitope peptides could elicit CTLs that can kill cancer cells expressing both CDC45L and HLA-A24. As CDC45L is strongly expressed in several kinds of human malignancies including lung, prostate, breast and bladder cancers, CDC45L is therefore suggested to be a promising target of peptide-based immunotherapy for malignancies described above, without causing any autoimmune phenomena.

Industrial Applicability

The present invention provides new TAAs, particularly those derived from CDC45L which may induce potent and specific anti-tumor immune responses and have applicability to a wide variety of cancer types. Such TAAs can find utility as peptide vaccines against diseases associated with CDC45L, e.g., cancer, examples of which include, but are not limited to, testicular tumor, pancreatic cancer, bladder cancer, non-small cell lung cancer, small cell lung cancer, breast cancer, esophageal cancer, prostate cancer, chronic myeloid leukemia (CML), soft tissue tumor, gastric cancer, hepatobiliary cancer, and colorectal cancer.

All patents, patent applications, and publications cited herein are incorporated by reference in their entirety.

Furthermore, while the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. An isolated peptide of less than 15 amino acids that has cytotoxic T lymphocyte (CTL) inducibility, wherein said peptide comprises an amino acid sequence selected from the group consisting of:
   (a) SEQ ID NOs: 4, 2, 3, 7 and 12; and
   (b) SEQ ID NOs: 4, 2, 3, 7 and 12, in which 1 or 2 amino acids are substituted and/or added.

2. The isolated peptide of claim 1, wherein said peptide has one or both of the following characteristics:
   (a) the second amino acid from the N-terminus is or is modified to be an amino acid selected from the group consisting of phenylalanine, tyrosine, methionine and tryptophan; and
   (b) the C-terminal amino acid is or is modified to be an amino acid selected from the group consisting of phenylalanine, leucine, isoleucine, tryptophan and methionine.

3. The isolated peptide of claim 1, wherein said peptide has one or both of the following characteristics:
   (a) the second amino acid from the N-terminus is or is modified to be an amino acid selected from the group consisting of leucine and methionine; and
   (b) the C-terminal amino acid is or is modified to be an amino acid selected from the group consisting of valine and leucine.

4. The isolated peptide of claim 1, wherein said peptide is a nonapeptide or decapeptide.

5. A composition for inducing a CTL, wherein the composition comprises one or more peptide(s) set forth in claim 1.

6. A pharmaceutical composition for the treatment of cancers in which CDC45L is overexpressed, wherein the composition comprises one or more peptide(s) set forth in claim 1.

7. The pharmaceutical composition of claim 6 formulated for the administration to a subject whose HLA antigen is HLA-A24 or HLA-A2.

8. A method for inducing an antigen-presenting cell (APC) with CTL inducibility, wherein the method comprises a step of contacting an APC with the peptide of claim 1 in vitro, ex vivo or in vivo.

9. A method for inducing a CTL, wherein the method comprises a step of co-culturing a CD8 positive T cell with an APC that presents on its surface a complex of an HLA antigen and the peptide of claim 1.

10. A diagnostic kit comprising the peptide of claim 1.

* * * * *

SEQUENCE LISTING

<160> NUMBER OF SEQ ID NOS: 26

<210> SEQ ID NO 1
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 1

Lys Tyr Val Thr Asp Val Gly Val Leu
1               5

<210> SEQ ID NO 2
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 2

Val Tyr Asn Asp Thr Gln Ile Lys Leu
1               5

<210> SEQ ID NO 3
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 3

Ser Tyr Thr Ala Ala Arg Phe Lys Leu
1               5

<210> SEQ ID NO 4
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 4

Lys Phe Leu Asp Ala Leu Ile Ser Leu
1               5

<210> SEQ ID NO 5
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 5

Lys Phe Gln Ala Met Asp Ile Ser Leu
1               5

<210> SEQ ID NO 6
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 6

His Phe Ile Gln Ala Leu Asp Ser Leu

```
<210> SEQ ID NO 7
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 7

Lys Phe Leu Ala Ser Asp Val Val Phe
1               5

<210> SEQ ID NO 8
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 8

Glu Tyr His Gly Thr Ser Ser Ala Met
1               5

<210> SEQ ID NO 9
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 9

His Phe Asp Leu Ser Val Ile Glu Leu
1               5

<210> SEQ ID NO 10
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 10

His Phe Gly Phe Lys His Lys Phe Leu
1               5

<210> SEQ ID NO 11
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 11

Val Tyr Asn Asp Thr Gln Ile Lys Leu Leu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 12

Lys Phe Leu Asp Ala Leu Ile Ser Leu Leu
1               5                   10
```

```
<210> SEQ ID NO 13
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 13

Ser Phe Glu Tyr Asp Leu Arg Leu Val Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 14

Glu Phe Leu Ala Asp Met Gly Leu Pro Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 15

Leu Phe Val Ala Ser Asp Val Asp Ala Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 16

Leu Phe Ser Arg Pro Ala Ser Leu Ser Leu
1               5                   10

<210> SEQ ID NO 17
<211> LENGTH: 1938
<212> TYPE: DNA
<213> ORGANISM: Homo sapiens

<400> SEQUENCE: 17
gatttggcgg gagtcttgac cgccgccggg ctcttggtac ctcagcgcga gcgccaggcg      60
tccggccgcc gtggctatgt tcgtgtccga tttccgcaaa gagttctacg aggtggtcca     120
gagccagagg gtccttctct tcgtggcctc ggacgtggat gctctgtgtg cgtgcaagat     180
ccttcaggcc ttgttccagt gtgaccacgt gcaatatacg ctggttccag tttctgggtg     240
gcaagaactt gaaactgcat tcttgagcat taagaacag tttcattatt ttattctcat     300
aaactgtgga gctaatgtag acctattgga tattcttcaa cctgatgaag acactatatt     360
ctttgtgtgt gacacccata ggccagtcaa tgtcgtcaat gtatacaacg atacccagat     420
caaattactc attaaacaag atgatgacct tgaagttccc gcctatgaag acatcttcag     480
ggatgaagag gaggatgaag agcattcagg aaatgacagt gatgggtcag agccttctga     540
gaagcgcaca cggttagaag aggagatagt ggagcaaacc atgcgaggga gcagcggcg      600
```

```
agagtgggag gcccggagaa gagacatcct ctttgactac gagcagtatg aatatcatgg    660
gacatcgtca gccatggtga tgtttgagct ggcttggatg ctgtccaagg acctgaatga    720
catgctgtgg tgggccatcg ttggactaac agaccagtgg gtgcaagaca agatcactca    780
aatgaaatac gtgactgatg ttggtgtcct gcagcgccac gtttcccgcc acaaccaccg    840
gaacgaggat gaggagaaca cactctccgt ggactgcaca cggatctcct ttgagtatga    900
cctccgcctg gtgctctacc agcactggtc cctccatgac agcctgtgca acaccagcta    960
taccgcagcc aggttcaagc tgtggtctgt gcatggacag aagcggctcc aggagttcct   1020
tgcagacatg ggtcttcccc tgaagcaggt gaagcagaag ttccaggcca tggacatctc   1080
cttgaaggag aatttgcggg aaatgattga agagtctgca aataaatttg ggatgaagga   1140
catgcgcgtg cagactttca gcattcattt tgggttcaag cacaagtttc tggccagcga   1200
cgtggtcttt gccaccatgt ctttgatgga gagccccgag aaggatggct cagggacaga   1260
tcacttcatc caggctctgg acagcctctc caggagtaac ctggacaagc tgtaccatgg   1320
cctggaactc gccaagaagc agctgcgagc cacccagcag accattgcca gctgcctttg   1380
caccaacctc gtcatctccc aggggccttt cctgtactgc tctctcatgg agggcactcc   1440
agatgtcatg ctgttctcta ggccggcatc cctaagcctg ctcagcaaac acctgctcaa   1500
gtccttttgtg tgttcgacaa agaaccggcg ctgcaaactg ctgcccctgg tgatggctgc   1560
cccctgagc atggagcatg gcacagtgac cgtggtgggc atcccccag agaccgacag   1620
ctcggacagg aagaactttt ttgggagggc gtttgagaag gcagcggaaa gcaccagctc   1680
ccggatgctg cacaaccatt tgacctctc agtaattgag ctgaaagctg aggatcggag   1740
caagtttctg gacgcactta tttccctcct gtcctaggaa tttgattctt ccagaatgac   1800
cttcttattt atgtaactgg ctttcattta gattgtaagt tatggacatg atttgagatg   1860
tagaagccat tttttattaa ataaaatgct tattttaggc tccgtcccca aaaaaaaaa   1920
aaaaaaaaaa aaaaaaaa                                                 1938
```

<210> SEQ ID NO 18
<211> LENGTH: 566
<212> TYPE: PRT
<213> ORGANISM: Homo sapiens

<400> SEQUENCE: 18

```
Met Phe Val Ser Asp Phe Arg Lys Glu Phe Tyr Glu Val Val Gln Ser
1               5                   10                  15

Gln Arg Val Leu Leu Phe Val Ala Ser Asp Val Asp Ala Leu Cys Ala
            20                  25                  30

Cys Lys Ile Leu Gln Ala Leu Phe Gln Cys Asp His Val Gln Tyr Thr
        35                  40                  45

Leu Val Pro Val Ser Gly Trp Gln Glu Leu Glu Thr Ala Phe Leu Glu
    50                  55                  60

His Lys Glu Gln Phe His Tyr Phe Ile Leu Ile Asn Cys Gly Ala Asn
65                  70                  75                  80

Val Asp Leu Leu Asp Ile Leu Gln Pro Asp Glu Asp Thr Ile Phe Phe
                85                  90                  95

Val Cys Asp Thr His Arg Pro Val Asn Val Asn Val Tyr Asn Asp
            100                 105                 110

Thr Gln Ile Lys Leu Leu Ile Lys Gln Asp Asp Leu Glu Val Pro
        115                 120                 125

Ala Tyr Glu Asp Ile Phe Arg Asp Glu Glu Glu Asp Glu Glu His Ser
    130                 135                 140
```

-continued

```
Gly Asn Asp Ser Asp Gly Ser Glu Pro Ser Glu Lys Arg Thr Arg Leu
145                 150                 155                 160

Glu Glu Glu Ile Val Glu Gln Thr Met Arg Arg Gln Arg Glu
            165                 170                 175

Trp Glu Ala Arg Arg Asp Ile Leu Phe Asp Tyr Glu Gln Tyr Glu
        180                 185                 190

Tyr His Gly Thr Ser Ser Ala Met Val Met Phe Glu Leu Ala Trp Met
            195                 200                 205

Leu Ser Lys Asp Leu Asn Asp Met Leu Trp Trp Ala Ile Val Gly Leu
    210                 215                 220

Thr Asp Gln Trp Val Gln Asp Lys Ile Thr Gln Met Lys Tyr Val Thr
225                 230                 235                 240

Asp Val Gly Val Leu Gln Arg His Val Ser Arg His Asn His Arg Asn
                245                 250                 255

Glu Asp Glu Glu Asn Thr Leu Ser Val Asp Cys Thr Arg Ile Ser Phe
            260                 265                 270

Glu Tyr Asp Leu Arg Leu Val Leu Tyr Gln His Trp Ser Leu His Asp
        275                 280                 285

Ser Leu Cys Asn Thr Ser Tyr Thr Ala Ala Arg Phe Lys Leu Trp Ser
    290                 295                 300

Val His Gly Gln Lys Arg Leu Gln Glu Phe Leu Ala Asp Met Gly Leu
305                 310                 315                 320

Pro Leu Lys Gln Val Lys Gln Lys Phe Gln Ala Met Asp Ile Ser Leu
                325                 330                 335

Lys Glu Asn Leu Arg Glu Met Ile Glu Glu Ser Ala Asn Lys Phe Gly
            340                 345                 350

Met Lys Asp Met Arg Val Gln Thr Phe Ser Ile His Phe Gly Phe Lys
        355                 360                 365

His Lys Phe Leu Ala Ser Asp Val Val Phe Ala Thr Met Ser Leu Met
    370                 375                 380

Glu Ser Pro Glu Lys Asp Gly Ser Gly Thr Asp His Phe Ile Gln Ala
385                 390                 395                 400

Leu Asp Ser Leu Ser Arg Ser Asn Leu Asp Lys Leu Tyr His Gly Leu
                405                 410                 415

Glu Leu Ala Lys Lys Gln Leu Arg Ala Thr Gln Gln Thr Ile Ala Ser
            420                 425                 430

Cys Leu Cys Thr Asn Leu Val Ile Ser Gln Gly Pro Phe Leu Tyr Cys
        435                 440                 445

Ser Leu Met Glu Gly Thr Pro Asp Val Met Leu Phe Ser Arg Pro Ala
    450                 455                 460

Ser Leu Ser Leu Leu Ser Lys His Leu Leu Lys Ser Phe Val Cys Ser
465                 470                 475                 480

Thr Lys Asn Arg Arg Cys Lys Leu Leu Pro Leu Val Met Ala Ala Pro
                485                 490                 495

Leu Ser Met Glu His Gly Thr Val Thr Val Val Gly Ile Pro Pro Glu
            500                 505                 510

Thr Asp Ser Ser Asp Arg Lys Asn Phe Phe Gly Arg Ala Phe Glu Lys
        515                 520                 525

Ala Ala Glu Ser Thr Ser Ser Arg Met Leu His Asn His Phe Asp Leu
    530                 535                 540

Ser Val Ile Glu Leu Lys Ala Glu Asp Arg Ser Lys Phe Leu Asp Ala
545                 550                 555                 560

Leu Ile Ser Leu Leu Ser
```

```
<210> SEQ ID NO 19
<211> LENGTH: 24
<212> TYPE: DNA
<213> ORGANISM: Artificial Sequence
<220> FEATURE:
<223> OTHER INFORMATION: A synthesized sense primer sequence for CDC45L

<400> SEQUENCE: 19
ctggtgttgc acaggctgtc atgg                                          24

<210> SEQ ID NO 20
<211> LENGTH: 21
<212> TYPE: DNA
<213> ORGANISM: Artificial Sequence
<220> FEATURE:
<223> OTHER INFORMATION: A synthesized antisense primer sequence for
      CDC45L

<400> SEQUENCE: 20
cgcacacggt tagaagagga g                                             21

<210> SEQ ID NO 21
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 21

Arg Tyr Leu Arg Asp Gln Gln Leu Leu
1               5

<210> SEQ ID NO 22
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 22

Ser Leu Tyr Asn Thr Tyr Ala Thr Leu
1               5

<210> SEQ ID NO 23
<211> LENGTH: 22
<212> TYPE: DNA
<213> ORGANISM: Artificial Sequence
<220> FEATURE:
<223> OTHER INFORMATION: A synthesized 5' primer sequence for TCR

<400> SEQUENCE: 23
gtctaccagg cattcgcttc at                                            22

<210> SEQ ID NO 24
<211> LENGTH: 24
<212> TYPE: DNA
<213> ORGANISM: Artificial Sequence
<220> FEATURE:
<223> OTHER INFORMATION: A synthesized 3' primer sequence for TCR alpha
      C region

<400> SEQUENCE: 24
tcagctggac cacagccgca gcgt                                          24

<210> SEQ ID NO 25
```

```
<211> LENGTH: 21
<212> TYPE: DNA
<213> ORGANISM: Artificial Sequence
<220> FEATURE:
<223> OTHER INFORMATION: A synthesized 3' primer sequence for TCR beta
      C1 region

<400> SEQUENCE: 25
tcagaaatcc tttctcttga c                                              21

<210> SEQ ID NO 26
<211> LENGTH: 24
<212> TYPE: DNA
<213> ORGANISM: Artificial Sequence
<220> FEATURE:
<223> OTHER INFORMATION: A synthesized 3' primer sequence for TCR beta
      C2 region

<400> SEQUENCE: 26
ctagcctctg gaatcctttc tctt                                           24
```